United States Patent
Oh et al.

(10) Patent No.: US 10,937,544 B2
(45) Date of Patent: *Mar. 2, 2021

(54) MEDICAL IMAGING APPARATUS FOR DISPLAYING X-RAY IMAGES OF DIFFERENT TYPES

(71) Applicant: SAMSUNG ELECTRONICS CO., LTD., Suwon-si (KR)

(72) Inventors: Hyun Hwa Oh, Hwaseong-si (KR); Young Hun Sung, Hwaseong-si (KR); Jae Hyun Kwon, Hwaseong-si (KR); Kang Eui Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/816,894

(22) Filed: Mar. 12, 2020

(65) Prior Publication Data

US 2020/0211702 A1 Jul. 2, 2020

Related U.S. Application Data

(63) Continuation of application No. 14/966,087, filed on Dec. 11, 2015, now Pat. No. 10,622,108, which is a (Continued)

(30) Foreign Application Priority Data

Oct. 4, 2013 (KR) .................. 10-2013-0118779

(51) Int. Cl.
*G16H 40/63* (2018.01)
*G16H 30/20* (2018.01)
(Continued)

(52) U.S. Cl.
CPC .......... *G16H 40/63* (2018.01); *G06F 3/0488* (2013.01); *G06T 3/40* (2013.01); *G06T 7/0012* (2013.01);
(Continued)

(58) Field of Classification Search
CPC ............ G06T 3/40; G06T 2207/10072; G06T 7/0012
See application file for complete search history.

(56) References Cited

U.S. PATENT DOCUMENTS 5,485,371 A 1/1996 Ito et al.
6,195,094 B1 2/2001 Celebiler
(Continued)

FOREIGN PATENT DOCUMENTS

CN 102117180 A 7/2011
EP 0913807 A2 5/1999
(Continued)

OTHER PUBLICATIONS

Communication dated Dec. 11, 2019, issued by the Korean Intellectual Property Office in counterpart Korean Application No. 10-2013-0118779.
(Continued)

*Primary Examiner* — Terrell M Robinson
(74) *Attorney, Agent, or Firm* — Sughrue Mion, PLLC

(57) ABSTRACT

Disclosed herein are a display apparatus which facilitates a simultaneous comparison of a plurality of images which respectively illustrate different features on one divided display screen such that the images are seamlessly displayed on the screen, and an image display method which is performable by using the apparatus. The display apparatus includes a memory configured to store a plurality of different types of images of an object, an input device configured to receive an input of a command relating to simultaneously displaying the different types of images, and a display device config-
(Continued)

ured to display images. Upon receiving the command, the display device divides a screen upon which an image of the object is displayable into a first region within which a first image showing one portion of the object is displayed and a second region within which a second image showing the remaining portion of the object is displayed.

10 Claims, 22 Drawing Sheets

Related U.S. Application Data continuation of application No. 14/505,686, filed on Oct. 3, 2014, now Pat. No. 10,468,134.

(51) Int. Cl.
| | | |
|---|---|---|
| *G06T 7/00* | (2017.01) | |
| *G06F 3/0488* | (2013.01) | |
| *G06T 3/40* | (2006.01) | |
| *G09G 5/14* | (2006.01) | |

(52) U.S. Cl.
CPC ............... *G09G 5/14* (2013.01); *G16H 30/20* (2018.01); *G06T 2200/24* (2013.01); *G06T 2207/10072* (2013.01); *G06T 2207/10116* (2013.01); *G09G 2340/12* (2013.01)

(56) References Cited

U.S. PATENT DOCUMENTS

| | | | |
|---|---|---|---|
| 6,239,799 | B1 | 5/2001 | Owings |
| 6,310,631 | B1 | 10/2001 | Cecco et al. |
| 6,914,958 | B2 | 1/2005 | Ganin |
| 8,627,228 | B2 | 1/2014 | Yosef et al. |
| 2004/0037468 | A1 | 2/2004 | Morishima et al. |
| 2006/0004275 | A1 | 1/2006 | Vija et al. |
| 2006/0018425 | A1 | 1/2006 | Nabatame |
| 2006/0020903 | A1 | 1/2006 | Wang et al. |
| 2006/0098897 | A1 | 5/2006 | Dewaele |
| 2007/0122021 | A1* | 5/2007 | Zingaretti ............. G06T 7/0014 382/132 |
| 2009/0225102 | A1* | 9/2009 | Okubo .................. G06F 19/321 345/661 |
| 2009/0257657 | A1 | 10/2009 | Temmermans et al. |
| 2010/0211409 | A1 | 8/2010 | Kotula et al. |
| 2011/0058653 | A1 | 3/2011 | Baumgart et al. |
| 2011/0125526 | A1 | 5/2011 | Gustafson |
| 2011/0135185 | A1* | 6/2011 | Gkanatsios ............ A61B 6/463 382/132 |
| 2011/0157154 | A1 | 6/2011 | Bernard et al. |
| 2011/0164802 | A1 | 7/2011 | Lin et al. |
| 2011/0255654 | A1 | 10/2011 | Kim et al. |
| 2012/0057674 | A1 | 3/2012 | Zhang |
| 2012/0069049 | A1 | 3/2012 | Howe et al. |
| 2012/0087557 | A1 | 4/2012 | Miller et al. |
| 2012/0294589 | A1 | 11/2012 | Samra et al. |
| 2012/0299967 | A1 | 11/2012 | Urabe |
| 2014/0037057 | A1 | 2/2014 | Kim |
| 2014/0121524 | A1 | 5/2014 | Chiang et al. |
| 2015/0002547 | A1 | 1/2015 | Itai |
| 2015/0150521 | A2* | 6/2015 | Roncalez ............... A61B 8/468 715/761 |
| 2015/0160821 | A1* | 6/2015 | Cho ..................... G06F 19/321 715/769 |
| 2015/0309712 | A1* | 10/2015 | Marshall ............. G06F 3/04817 715/765 |

FOREIGN PATENT DOCUMENTS

| | | | |
|---|---|---|---|
| EP | 2484275 | A1 | 8/2012 |
| JP | 61160795 | A | 7/1986 |
| JP | 63223968 | A | 9/1988 |
| JP | 0199083 | A | 4/1989 |
| JP | 2006095279 | A | 4/2006 |
| JP | 2013085967 | A | 5/2013 |
| KR | 10-2013-0043974 | A | 5/2013 |
| TW | 200604920 | A | 2/2006 |
| WO | 2004034910 | A1 | 4/2004 |
| WO | 2010/096438 | A3 | 8/2010 |
| WO | 2010096438 | A2 | 8/2010 |

OTHER PUBLICATIONS

Communication dated Jul. 2, 2019, issued by the Japanese Patent Office in counterpart Japanese Application No. 2014-197324.
Communication dated Jul. 19, 2019, issued by the European Patent Office in counterpart European Application No. 17 167 330.4.
Communication dated Jul. 24, 2019, issued by the Indian Patent Office in counterpart Indian Application No. 2767/DEL/2014.
Communication dated Aug. 1, 2019, issued by the European Patent Office in counterpart European Application No. 16 160 808.8.
Communication dated Feb. 21, 2019, issued by the European Patent Office in counterpart European Application No. 17167330.4.
Communication dated Jan. 24, 2019, issued by the State Intellectual Property Office of P.R. China in counterpart Chinese Application No. 201410525012.6.
Communication issued Aug. 4, 2017 by the European Patent Office in counterpart European Patent Application No. 17167330.4.
Communication dated Oct. 16, 2018 issued by the Japanese Patent Office in counterpart Japanese Application No. 2014-197324.
Communication dated Aug. 14, 2018, issued by the State Intellectual Property Office of P.R. China in counterpart Chinese Application No. 201410525012.6.
Communication dated Feb. 9, 2018, issued by the European Patent Office in counterpart EP app No. 16 160 808.8.
Communication dated Dec. 14, 2016 issued by the European Patent Office in counterpart European Patent Application No. 14 187 055.0.
Communication dated Dec. 14, 2016 issued by the European Patent Office in counterpart European Patent Application No. 14 187 055.0 (Decision to Refuse).
Anonymous; "New WinSplitter Control"; INFRAGISTICS; (http://help.infragistics.com/doc/winForms/2012.1/CLR2.0/); Dec. 31, 2012; XP055224181; 1 pg. total.
Zurb et al; "jQuery TwentyTwenty Plugin | Playground from ZURB"; Internet Archive WayBackMachine; Sep. 22, 2013; (https://web.archive.org/web/20130922044238/http:/zurd.com/playground/twentytwenty); XP055308800; 6 pgs. total.
Anonymous; "WordPress—Multipurpose Before After Slider | CodeCanyon"; (https://web.archive.org/web/20130715070127/http:/codecanyon.net/item/multipurpose-before-after-slider/5159016; XP055308799; 6 pgs. total.
Communication dated May 18, 2016, issued by the European Patent Office in counterpart European Patent Application No. 14187055.0.
Communication dated Jul. 15, 2016, issued by the European Patent Office in counterpart European Patent Application No. 1610808.8.
Communication dated Nov. 6, 2015, issued by the European Patent Office in counterpart European Application No. 14187055.0.
Anonymous: "New WinSplitter Control", Dec. 31, 2012, XP055224181, Total 2 pages, URL: http://help.infragistics.com/doc/WinForms/2012.1/CLR2.0/.
Communication dated Jan. 7, 2015 by the European Patent Office in related application 14187055.0.
Communication dated May 26, 2020 by the Japanese Patent Office in counterpart Japanese Patent Application No. 2014-197324.
Communication dated Aug. 11, 2020 by the European Patent Office in counterpart European Patent Application No. 16160808.8.
Communication dated Sep. 3, 2020 by the European Patent Office in counterpart European Patent Application No. 20175609.5.

* cited by examiner

MEDICAL IMAGING APPARATUS FOR DISPLAYING X-RAY IMAGES OF DIFFERENT TYPES

CROSS-REFERENCE TO RELATED APPLICATIONS

This is a continuation application of U.S. patent application Ser. No. 14/996,087, filed Dec. 11, 2015, in the U.S. Patent and Trademark Office, which application is a continuation of U.S. patent application Ser. No. 14/505,686, filed on Oct. 3, 2014, and issued as U.S. Pat. No. 10,468,134, on Nov. 5, 2019, in the United States Patent and Trademark Office, which claims priority from Korean Patent Application No. 10-2013-0118779, filed on Oct. 4, 2013 in the Korean Intellectual Property Office, the disclosures of which are incorporated herein by reference in their entireties.

BACKGROUND

1. Field

Exemplary embodiments relate to a display apparatus which is usable for displaying images.

2. Description of the Related Art

When images are checked by using display apparatuses, it is sometimes necessary to compare the images. In the field of medicine, where images of a patient are often obtained by using multiple medical imaging apparatuses in order to find lesions, the comparison may be necessary. Generally, in order to compare multiple images which have been obtained by using various types of medical imaging apparatuses, the images to be checked are displayed on multiple display apparatuses.

In the case that multiple display apparatuses are used, it may be relatively difficult, compared to the case of using one display apparatus, to promptly compare the images of a region of interest. Further, because the region of interest must be checked by shifting focus from one display apparatus to another, it may be possible that a user, such as a physician and/or a medical professional, will become distracted or lose concentration.

SUMMARY

Therefore, it is an aspect of one or more exemplary embodiments to provide a display apparatus which facilitates a simultaneous comparison of multiple images on a divided screen and an image display method which is executable by using the display apparatus.

Additional aspects of the exemplary embodiments will be set forth in part in the description which follows and, in part, will be apparent from the description, or may be learned by practice of the exemplary embodiments.

In accordance with one aspect of one or more exemplary embodiments, a display apparatus includes a memory configured to store a plurality of different respective types of images of an object, an input device configured to receive an input of a command which relates to simultaneously displaying the different types of images, and a display device configured to display images, wherein, upon receiving the input of the command, the display device is further configured to divide a screen upon which an image of the object is displayable into a first region within which a first image showing one portion of the object is displayed and a second region within which a second image showing a remaining portion of the object is displayed.

In accordance with another aspect of one or more exemplary embodiments, a display apparatus includes a memory configured to store a plurality of different respective types of images of an object, an input device configured to receive an input of one of a division command and a shift command, and a display device configured to display images, wherein the display device is further configured to divide, when the division command is received, a screen upon which an image of the object is displayable into a first region within which a first image showing one portion of the object is displayed and a second region within which a second image showing a remaining portion of the object is displayed, and wherein the display device is further configured to shift, when the shift command is received, a boundary between the first region and the second region based on the shift command, and to change at least one from among relative screen shares of the first region and the second region and a respective proportional amount of the corresponding portion of the object shown in each of the first image and the second image based on the shift command.

In accordance with another aspect of one or more exemplary embodiments, an image display method which is executable by using a display apparatus includes receiving, by an input device, an input of a screen division command which relates to dividing a screen of a display device, and dividing the screen upon which an image of the object is displayable into a first region within which a first image showing one portion of the object is displayed and a second region within which a second image showing a remaining portion of the object is displayed based on the screen division command.

In accordance with a further aspect of one or more exemplary embodiments, an image display method for displaying a plurality of images showing a specific region of an object includes seamlessly displaying one portion of each of the images on a display device such that the displayed portions of the images showing the specific region of the object are combined to form a combination image of the specific region of the object.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
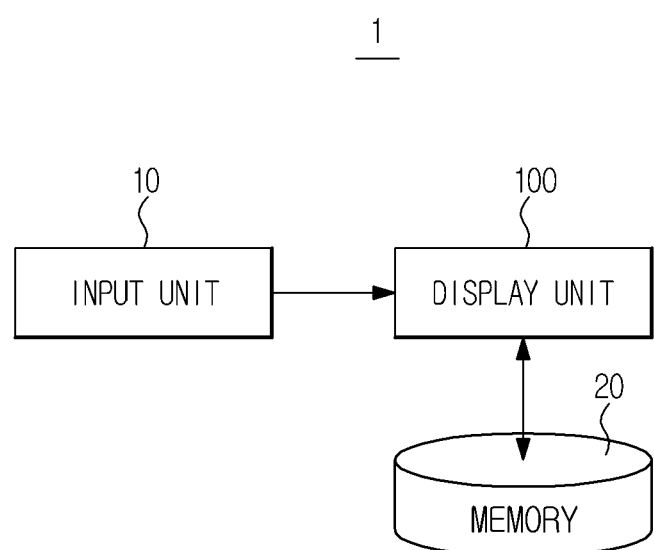
FIG. 1 is a view which illustrates an exemplary configuration of a display apparatus, according to an exemplary embodiment.

Reference will now be made in detail to the exemplary embodiments, examples of which are illustrated in the accompanying drawings, wherein like reference numerals refer to like elements throughout.

FIG. 1 is a view which illustrates an exemplary configuration of a display apparatus. The display apparatus 1 includes a display unit (also referred to herein as a "display device" and/or as a "display") 100 configured to display an image, a memory 20 configured to store images of an object which is displayed on the display unit 100, and an input unit (also referred to herein as an "input device") 10 configured to receive an input of a command which relates to a manipulation of the display apparatus 1. The display apparatus 1 according to an exemplary embodiment, which refers to a concept which covers any or all of various types of devices which are capable of displaying images, may include any one or more of a desktop computer, a laptop computer, a tablet computer, and a smartphone.

The display unit 100, which is a constituent of the display apparatus 1 and which includes a screen configured to display an image, may be implemented with any one or more of various kinds of commonly known display techniques. In addition, the display unit 100 may be implemented using a touchscreen configured to enable a user to input a command by directly touching the display unit 100, as well as via the input unit 10. The user is able to input a desired command to the display apparatus 1 by touching the display unit 100 with a finger or a touch pen (e.g., a stylus). The input unit 10 may include any one or more of a keyboard, a mouse, a joystick, a track ball, a jog wheel, a voice recognition device, and a motion recognition device. The input unit 10 may be integrated with the display apparatus 1 or installed in the display apparatus 1. Alternatively, the input unit may be provided separately from the display apparatus. In the case that the input unit is provided separately from the display apparatus, the input unit 10 may transmit a received command to the display apparatus via wireless communication, or may be connected to the display apparatus via any one or more of various kinds of connectors. When checking images via the display apparatus 1, the user sometimes needs to check images of the same object, and/or to check a specific region of the same object for which a corresponding image has been captured by using different techniques. In particular, this process is often necessary in the field of medicine. In the field of medicine, any one or more of various modalities, such as an x-ray apparatus, an ultrasound apparatus, a computed tomography apparatus, a magnetic resonance imaging apparatus, a positron emission tomography apparatus, and a single photon emission computed tomography apparatus, may be used to diagnose a disease. Each modality uses one or more of various kinds of imaging techniques to photograph an object. For example, by using predetermined various imaging techniques, the x-ray apparatus may obtain any one or more of a general x-ray image which shows all bones and soft tissues such as organs of the object, a bone x-ray image which shows only bones, a soft tissue x-ray image which shows only soft tissues such as organs, and a color x-ray image which provides a sharp contrast of colors.

The medical staff compares medical images of an object which are captured via various techniques of modalities as described above in order to check a region which is suspected of having a lesion. For a purpose of comparing various types of medical images with one another, multiple display apparatuses are generally used. However, using a single display apparatus to simultaneously compare various types of medical images may ensure a more intuitive and efficient comparison. Accordingly, disclosed exemplary embodiments provide a user interface which facilitates a simultaneous checking and comparison of a plurality of medical images which have been captured by using different techniques on a single display apparatus and a display apparatus which includes such a user interface. Hereinafter, exemplary embodiments will be described in a context which relates to x-ray images used for medical diagnosis. However, the technical spirit of the exemplary embodiments is not limited to medical images, and is rather applicable to any and all fields for which a comparison and analysis of a plurality of images is useful.

Figure 2:
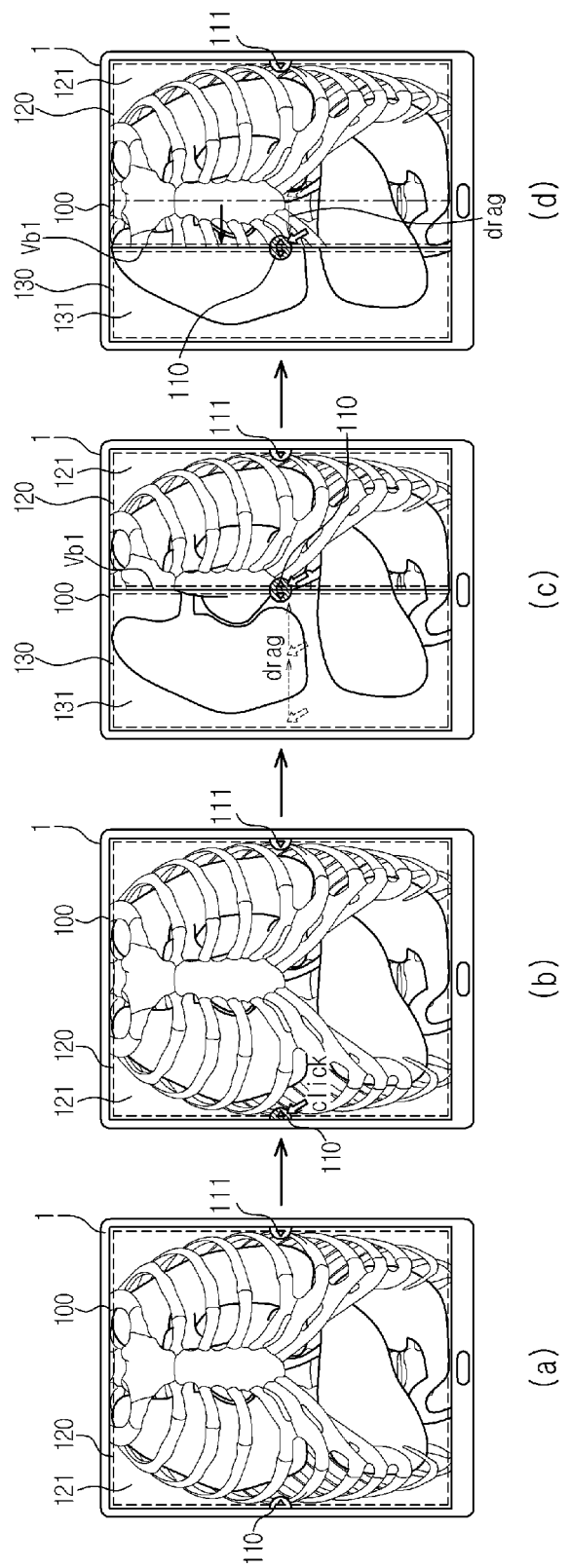
FIGS. 2, 3, 4, 5, 6, 7, 8, 9, 10, 11, 12, 13, and 14 are views which illustrate an exemplary method for dividing the screen of a display apparatus and displaying an image thereon.
Figure 3:
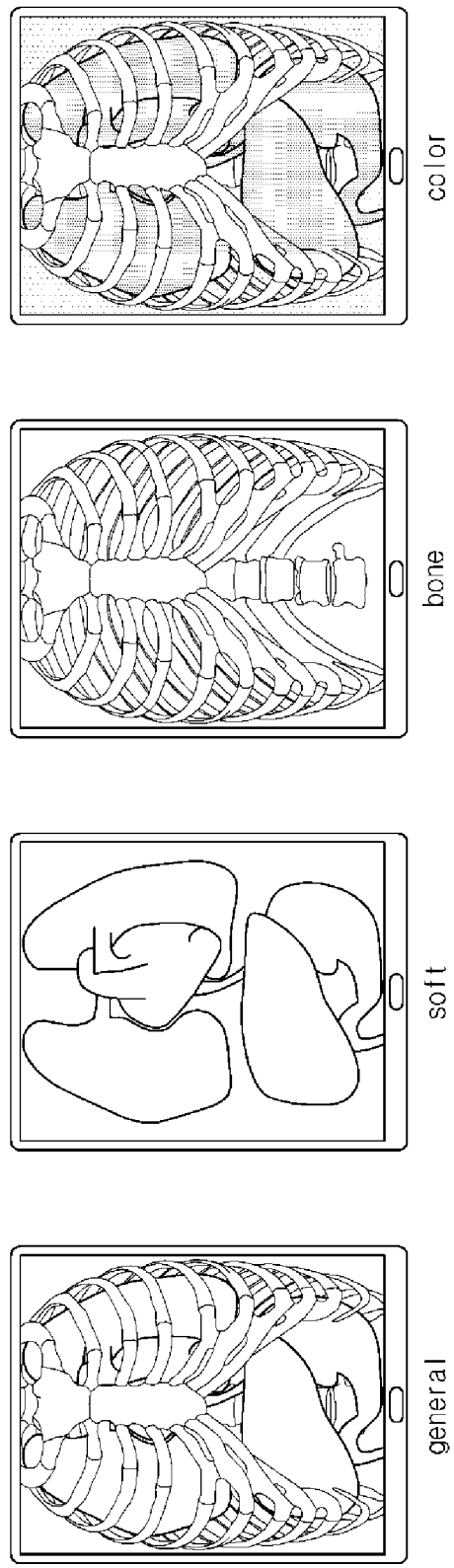

FIG. 2 illustrates an exemplary process for dividing the screen of a display unit, and FIG. 3 shows a general x-ray image (general), a soft tissue x-ray image (soft), bone x-ray image (bone), and a color x-ray image (color) as examples of x-ray images.

Referring to drawing (a) of FIG. 2, a captured general x-ray image of the chest region of an object is displayed on the display unit 100, and markers 110 and 111 which are usable for effecting a division of the screen are respectively displayed on the left and right sides of the display unit 100. The x-ray image is an example of a medical image. Medical images that may be displayed on the display unit 100 are not limited to x-ray images, but include images which may be captured via other kinds of modalities, such as an ultrasound apparatus, a computed tomography apparatus, a magnetic resonance imaging apparatus, a positron emission tomography apparatus, and a single photon emission computed tomography apparatus.

Drawing (a) of FIG. 2 shows a display region of the display unit 100 prior to an implementation of a screen division. A first region 120, in which a first image 121 which correspond to a general x-ray image is displayed, accounts for the entire display region of the display unit 100. The first image 121, which is displayed in the first region 120 prior to an implementation of a screen division, may be utilized as a reference image to be compared with other images which have been captured by using different techniques. Accordingly, the general x-ray image shown in FIG. 3 may be displayed as the first image 121. However, exemplary embodiments are not limited thereto. Various types of images which may be acquired by capturing images of a specific region of the same body by using different techniques, such as the bone x-ray image, the soft tissue x-ray image, and/or the color x-ray image of the same object shown in FIG. 3, may be selected and displayed by a user.

When the user clicks the marker 110 which is displayed on the left side of the display unit 100, as shown in drawing (b) of FIG. 2, and a command which implements a dragging of the marker 110 to the right side is received, as shown in drawing (c) of FIG. 2, the screen is divided into the first region 120 and a second region 130. When the marker 110 is clicked, a vertical boundary line vb1 which passes through the marker 110 is created. When the marker 110 is dragged, the vertical boundary line vb1 moves together with the marker 110 in the direction in which the marker 110 is dragged. The vertical boundary line vb1 serves as a boundary between the first region 120 and the second region 130.

As shown in drawings (a), (b), (c), and (d) of FIG. 2, the direction in which the marker 110 is movable may be indicated by a symbol, such as, for example, an arrow. In addition, clicking and dragging of the marker 110 may be performed via the aforementioned input unit 10, which may include any one or more devices, such as a mouse, a keyboard, a track ball, a joystick, jog wheel, a voice recognition device, and a motion recognition device.

As shown in drawing (c) of FIG. 2, when the vertical boundary line vb1 is moved to the right side by clicking the marker 110 and dragging the same to the right side of the display unit 100, the screen share of the first region 120 decreases, and the screen share of the second region 130 is newly created and increases. As the screen share of the first region 120 decreases, the proportional amount of the chest region of the object on the first image 121 displayed in the first region 120 also correspondingly decreases. In drawing (a) of FIG. 2, the entirety of the object is shown as the first image 121. In drawing (c) of FIG. 2, only the right half of the chest region of the object is displayed as the first image, and the left half of the chest region is displayed in the second region 130 as a second image 131. The combination of the first region 120, within which the first image 121 is displayed, and the second region 130, within which the second image 131 is displayed, represents the entirety of the chest region of the object.

As shown in drawing (d) of FIG. 2, when the vertical boundary line vb1 is moved inwardly with respect to the second region 130 by clicking the marker 110 and dragging the same toward the second region 130, the decreased screen share of the first region 120 increases, while the increased screen share of the second region 130 decreases. As the screen share of the first region 120 increases, the proportional amount of the chest region of the object shown in the first image 121 displayed in the first region 120 also correspondingly increases. In drawing (c) of FIG. 2, the first image 121 shows only the right half of the chest region of the object. Conversely, in drawing (d) of FIG. 2, the first image 121 shows approximately ⅔ of the object, and the remaining ⅓ of the object is shown on the second image 131 in the second region 130. Similar to drawing (c) of FIG. 2, in drawing (d) of FIG. 2, the combination of the first region 120 displaying the first image 121 and the second region 130 displaying the second image 131 represents the entire chest region of the object.

As shown in drawings (c) and (d) of FIG. 2, the second image 131 is an x-ray image of the same region or section of the same object. Specifically, the second image 131 is a soft tissue x-ray image which shows soft tissue of the object but does not show bones (see. e.g., the drawing labeled "soft" in FIG. 3). The soft tissue x-ray image is simply an example, and the second image 131 may include any one or more of various images which may be acquired by photographing the same section of the object as that represented by the first image 121 by using other imaging techniques.

As shown in drawings (c) and (d) of FIG. 2, the screen shares of the first region 120 and the second region 130 vary based on a corresponding movement of the marker 110, and thereby the proportional amounts of the object regions shown in the first image 121 and the second image 131 vary. However, regardless of the proportional amounts of the object region shown in the first image 121 and the second image 131, the first image 121 and the second image 131 naturally match with each other at the vertical boundary line vb1. The images matching with each other as above represent the entire image of the photographed region of the object, similarly as in the case of the image prior to screen division.

Using this method, the user may move the marker 110 near the region of interest, and thus may easily and quickly check the first image 121 and the second image 131 for the region of interest in an alternating manner. In particular, the user may seamlessly compare different types of images of the region of interest which have been captured by using different techniques, thus displaying unique information on a single display apparatus, rather than on a plurality of separate display apparatuses. Because it is possible to seamlessly check multiple images of the same region on one display apparatus 1 at the same time, an accuracy of diagnosis may be enhanced, and a more intuitive diagnosis may be possible.

Figure 4:
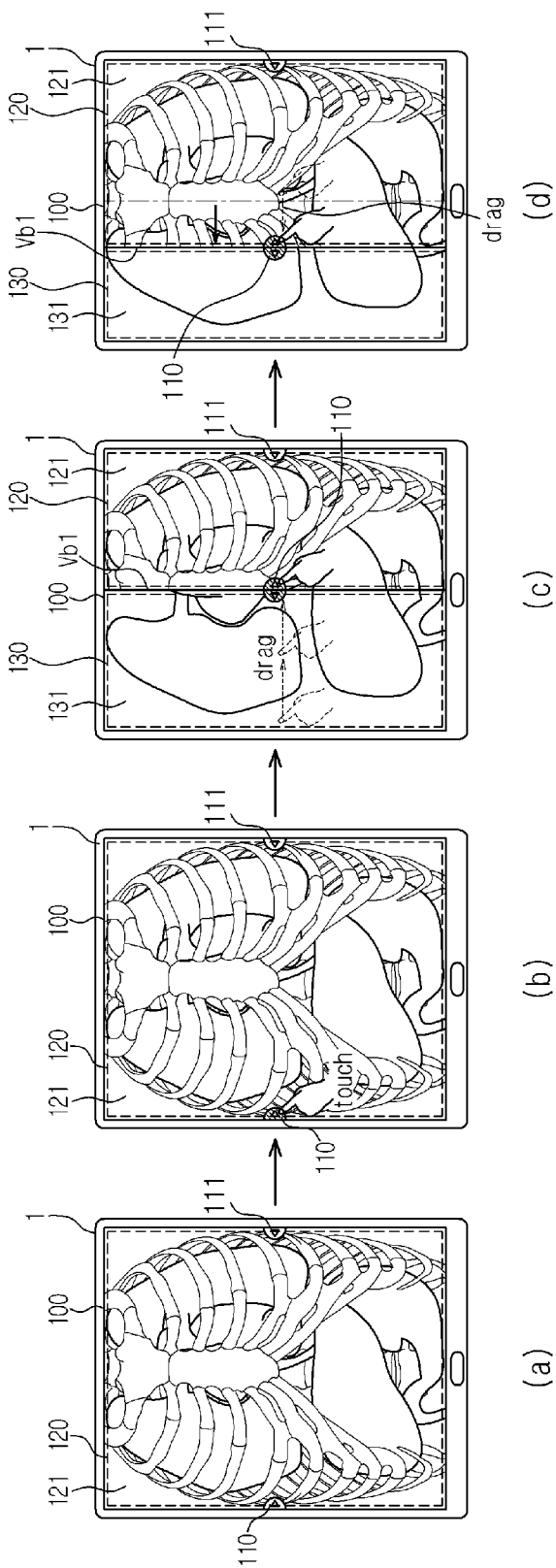

FIG. 4 illustrates an exemplary process for dividing the screen of the display unit by directly touching the display unit. The exemplary embodiment illustrated in FIG. 4 differs from the exemplary embodiment of FIG. 2 in that the marker 110 of the display unit 100 is touched using a touch tool, such as, for example, a finger or a touch pen. The display unit 100 may use any one or more of various kinds of commonly known touchscreens in order to facilitate input of a command by touch. Other technical details except this difference are the same as those of the exemplary embodiment of FIG. 2, and thus a description thereof will be omitted.

Figure 5:
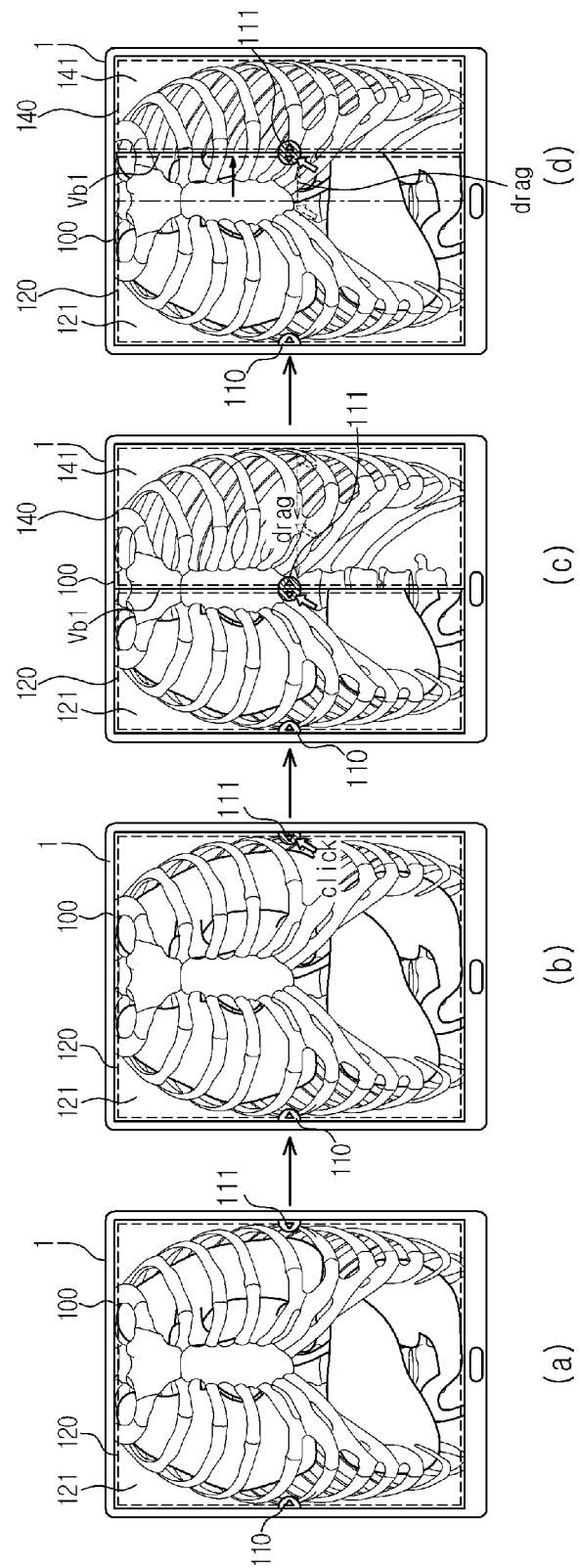

FIG. 5 illustrates another exemplary process for dividing the screen of the display unit. The exemplary embodiment illustrated in FIG. 5 differs from the embodiment of FIG. 2 in that the right marker 111 is clicked and moved and a bone x-ray image (see the drawing labeled "bone" in FIG. 3) is used as a second image 141 to be displayed on a second region 140. Other technical details except this difference are the same as those of the exemplary embodiment of FIG. 2, and thus a description thereof will be omitted.

When the user desires to observe the object by comparing a general x-ray image with a soft tissue x-ray image, the user may divide the screen by dragging the marker 110 displayed on the left side of the display unit 100, as shown in FIG. 2. When the user desires to observe the object by comparing the general x-ray image and a bone x-ray image, the user may divide the screen by dragging the marker 111 displayed on the right side of the display unit 100, as shown in FIG. 5. The images displayed in the second regions 130 and 140 of the divided screen may be replaced with a different type of images. The image displayed in the first region 120 may also be replaced with a different type of image. This will be described below with reference to FIGS. 16, 17, 18, and 19.

Figure 6:
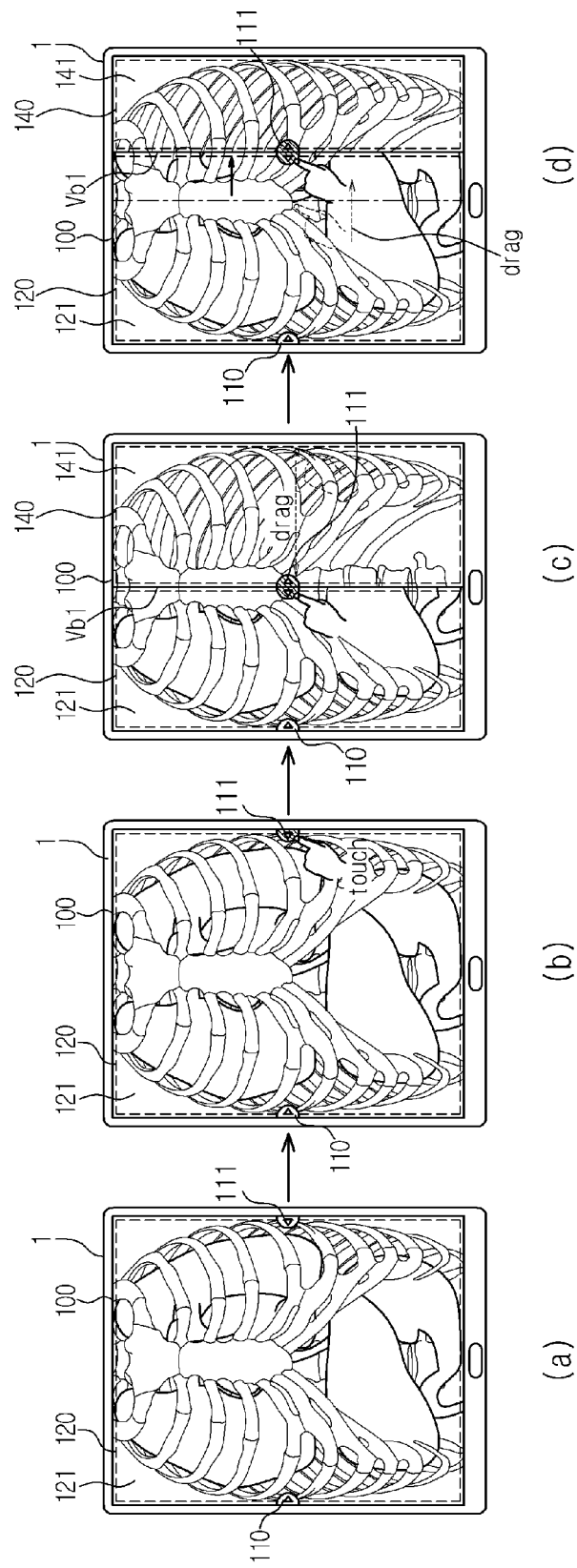

FIG. 6 illustrates another exemplary process for dividing the screen by directly touching the display unit. The exemplary embodiment illustrated in FIG. 6 differs from the exemplary embodiment of FIG. 5 in that the marker 111 of the display unit 100 is touched by using a touch tool, such as a finger or a touch pen. The display unit 100 may use any one or more of various kinds of commonly known touchscreens in order to facilitate input of a command by touch. Other technical details except this difference are the same as those of the exemplary embodiment of FIG. 5, and thus a description thereof will be omitted.

Figure 7:
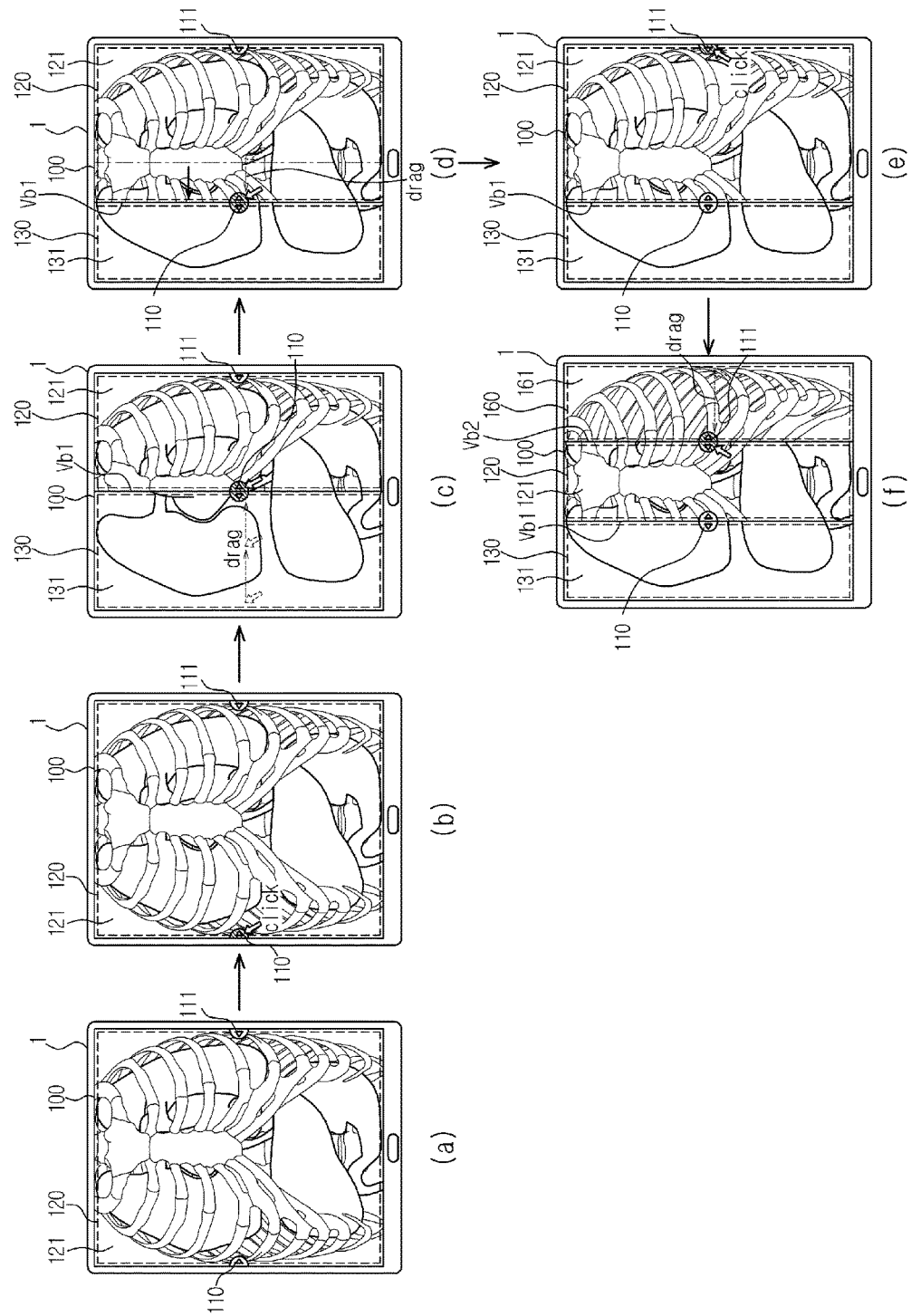

FIG. 7 illustrates another exemplary process for dividing the screen of the display unit into three regions.

Drawings (a), (b), (c), and (d) of FIG. 7 are respectively identical to drawings (a), (b), (c), and (d) of FIG. 2, and thus a description thereof will be omitted.

When the marker 111 displayed on the right side of the display unit 100 is clicked, as shown in drawing (e) of FIG. 7, and dragged to the left side in the clicked state, as shown in drawing (f) of FIG. 7, the screen is divided into a first region 120, which is at the center, and a second region 130 and a third region 160, which are separately arranged on the left and right sides, respectively. When the marker 111 is clicked, a vertical boundary line vb2 which passes through the marker 111 is created. When the marker 111 is dragged, the vertical boundary line vb2 moves together with the marker 111 in the dragging direction of the marker 111.

As shown in drawing (f) of FIG. 7, when the marker 111 displayed on the right side of the display unit 100 is clicked and dragged, a new vertical boundary line vb2 which corresponds to the boundary between the first region 120 and the newly produced third region 160 is created. The vertical boundary line vb2 moves together with the marker 111 in the dragging direction of the marker 111. When the new vertical boundary line vb2 is moved to the left by clicking the marker 111 displayed on the right side of the display unit 100 and dragging the same to the left side of the display unit 100, the screen share of the first region 120 with respect to a total screen area of the screen of the display unit 100 decreases, while the screen share of the newly produced third region 160 increases. When the screen share of the first region 120 decreases, the proportional amount of the object on the first image 121 displayed in the first region 120 also correspondingly decreases. In drawing (e) of FIG. 7, the first image 121 shows approximately ⅔ of the object. Conversely, in drawing (f) of FIG. 7, the first image 121 shows only approximately ⅓ of the object, and the remaining approximately ⅓ of the object is shown in a third image 161 which is displayed in the newly produced third region 160. The combination of the first region 120 displaying the first image 121, the second region 130 displaying the second image 131, and the third region 160 displaying the third image 161 represents the entire chest region of the object. The first image 121, the second image 131, and the third image 161 match with each other to seamlessly display the entirety of the chest region of the object.

Regarding the images displayed in the respective divided regions, a soft tissue x-ray image of the object is displayed in the second region 130 on the left side of the screen, a general x-ray image of the object is displayed in the first region 120 at the center of the screen, and a bone x-ray image of the object is displayed in the third region 160 on the right side of the screen, as shown in drawing (f) of FIG. 7. In particular, the images displayed in the three divided regions shown in drawing (f) of FIG. 7 are x-ray images of the same region of the same object. However, the images are captured by using different imaging techniques, and thus show different respective features of the object. The images displayed in different regions, however, may not be captured by using different techniques. For example, the images displayed in the second region 130 and the third region 160 in drawing (f) of FIG. 7 may be images which have been captured by using the same technique (e.g., soft tissue x-ray images or bone x-ray images).

The screen shares of the first region 120, the second region 130, and the third region 160 vary based on corresponding movements of the markers 110 and 111, and thereby the proportional amounts of the object shown in the first image 121, the second image 131, and the third image 161 vary. However, regardless of respective changes in proportional amounts of the object shown in the first image 121, the second image 131, and the third image 161, the first image 121, the second image 131, and the third image 161 naturally match with each other at the vertical boundary lines vb1 and vb2. Accordingly, the images in coordination with each other as above represent the entire image of the photographed region of the object, similarly as in the case of the image prior to screen division.

As described above, by using this method, the user may move the two markers 110 and 111 near the region of interest as shown in FIG. 7, and thus may easily and quickly check each of the first image 121, the second image 131, and the third image 161 of the region of interest in an alternating manner. In particular, the user may easily and seamlessly compare different types of images of the region of interest which have been captured by using different respective techniques, thus having unique information on one single display apparatus rather than on a plurality of display apparatuses in an alternating manner.

While FIGS. 2 and 7 respectively illustrate the screen as being divided into two regions and three regions, the screen may be divided into more than three regions. Because it is possible to simultaneously check multiple images of the same region of an object by dividing the screen into multiple regions on one single display apparatus, an accuracy of diagnosis may be enhanced, and a more intuitive diagnosis may be possible.

Figure 8:
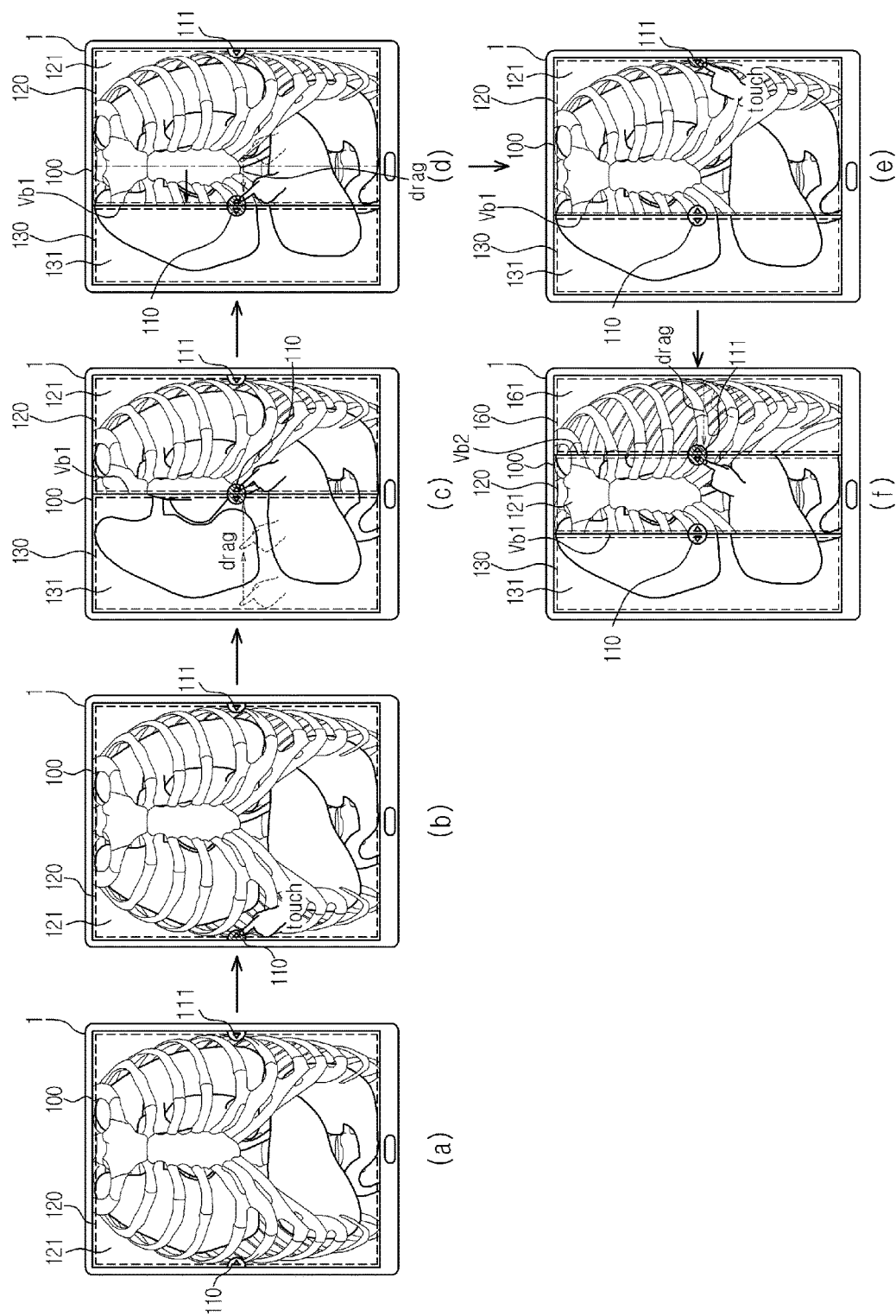

FIG. 8 illustrates another exemplary process for dividing the screen of the display unit into three regions.

The exemplary embodiment illustrated in FIG. 8 differs from the exemplary embodiment of FIG. 7 in that the markers 110 and 111 of the display unit 100 are touched using a touch tool, such as a finger or a touch pen. The display unit 100 may use any one or more of various kinds of commonly known touchscreens in order to facilitate input of a command by touch. Other technical details except this difference are the same as those of the exemplary embodiment of FIG. 7, and thus a description thereof will be omitted.

Figure 9:
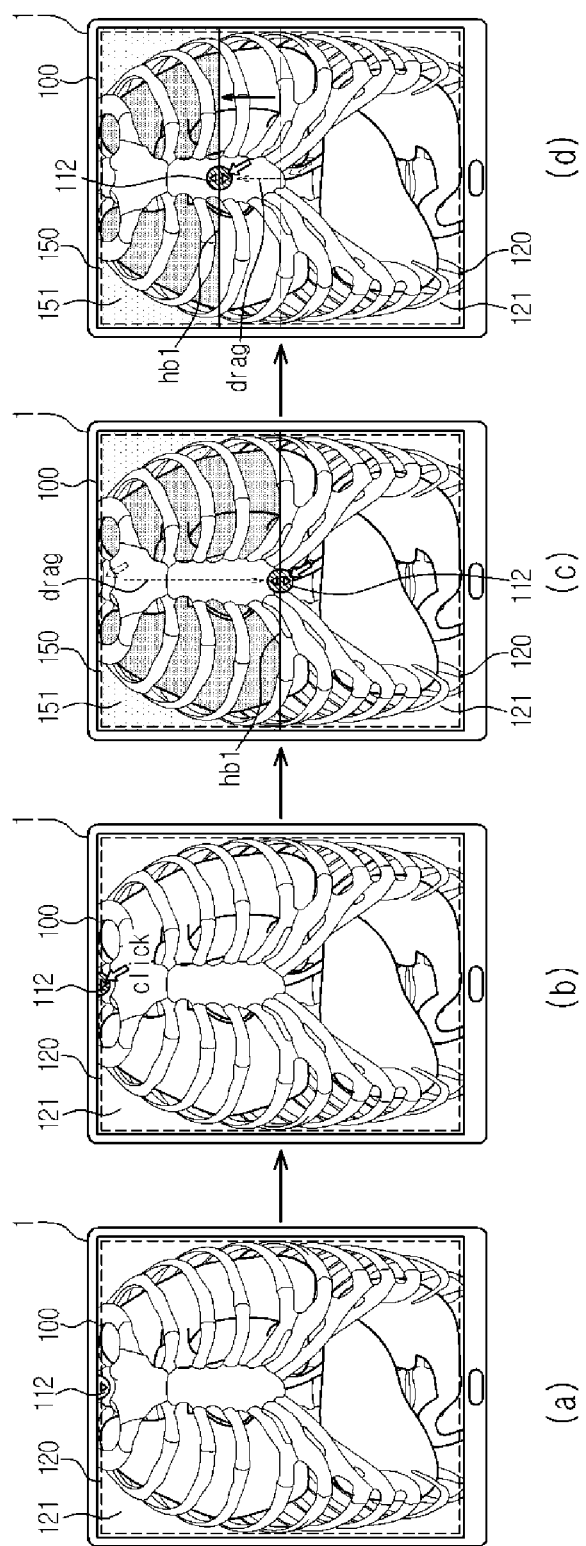

FIG. 9 illustrates another exemplary process for horizontally dividing the screen of the display unit.

Referring to drawing (a) of FIG. 9, the display unit 100 displays a general x-ray image which has been obtained by photographing the chest region of an object, and a marker 112 which is usable for indicating a division of the screen is displayed on the upper side of the screen of the display unit 100.

When the marker 112 displayed on the upper side of the screen of the display unit 100 is clicked as shown in drawing (b) of FIG. 9, and dragged down in the clicked state as shown in drawing (c) of FIG. 9, the screen is divided into a first region 120 and a second region 150. When the marker 112 is clicked, a horizontal boundary line hb1 which passes through the marker 112 is created. When the marker 112 is dragged, the horizontal boundary line hb1 moves together with the marker 112 in the dragging direction of the marker 112. The horizontal boundary line hb1 corresponds to the boundary between the first region 120 and the second region 150.

When the horizontal boundary line hb1 is moved down by clicking the marker 112 and dragging the same downward with respect to the display unit 100, the screen share of the first region 120 on the screen of the display unit 100 decreases, while the screen share of the newly produced second region 150 increases. As the screen share of the first region 120 decreases, the proportional amount of the chest region of the object shown in the first image 121 displayed in the first region 120 also correspondingly decreases. In drawing (a) of FIG. 9, the first image 121 shows the entire chest region of the object. Conversely, in drawing (c) of FIG. 9, only about a lower half of the chest region of the object is displayed via the first image 121. The upper half of the chest region is shown in the second image 151, which is displayed in the second region 150. The combination of the first region 120 displaying the first image 121 and the second region 150 displaying the second image 151 represents the entire chest region of the object, and the first image 121 and the second image 131 match with each other, thereby enabling the entire chest region of the object to be seamlessly displayed.

As shown in drawing (d) of FIG. 9, when the horizontal boundary line hb1 is moved toward the top of the second region 150 by clicking the marker 112 and dragging the same toward the top of the second region 150, the decreased screen share of the first region 120 increases, while the increased screen share of the second region 150 decreases. As the screen share of the first region 120 increases, the proportional amount of the object on the first image 121 displayed in the first region 120 also correspondingly increases. In drawing (c) of FIG. 9, the first image 121 shows only the lower half of the object. Conversely, in drawing (d) of FIG. 9, approximately ⅔ of the object is shown in the first image 121. The remaining approximately ⅓ of the object is shown in the second image 151, which is displayed in the second region 150. However, the combination of the first image 121 and the second image 151 shows the entire chest region of the object, similarly as in drawing (c) of FIG. 9.

As shown in drawings (c) and (d) of FIG. 9, the second image 151 is an x-ray image of the same region of the same object, but this image is a color x-ray image (see the drawing labeled "color" in FIG. 3), not a gray image. The color x-ray image is simply an example, and the second image 151 may include any one or more of images which may be acquired by photographing the same region of the object as that shown in the first image 121 by using different respective imaging techniques.

As shown in drawings (c) and (d) of FIG. 9, the respective screen shares of the first region 120 and the second region 150 vary based on a movement of the marker 112, and thereby the proportional amounts of the regions of the object shown in the first image 121 and the second image 151 vary. However, regardless of changes in proportional amounts of the regions of the object shown in the first image 121 and the second image 151, the first image 121 and the second image 151 naturally match with each other at the horizontal boundary line hb1. The image obtained through coordination represents the image of the entire photographed region of the object, similarly as the image prior to dividing of the screen. By manipulating the marker 112 which is displayed on the upper side of the screen in addition to the markers 110 and 111 of FIG. 7 which are displayed on the left and right sides of the screen, which are not shown in FIG. 9, the screen may be divided into four or six regions.

Figure 10:
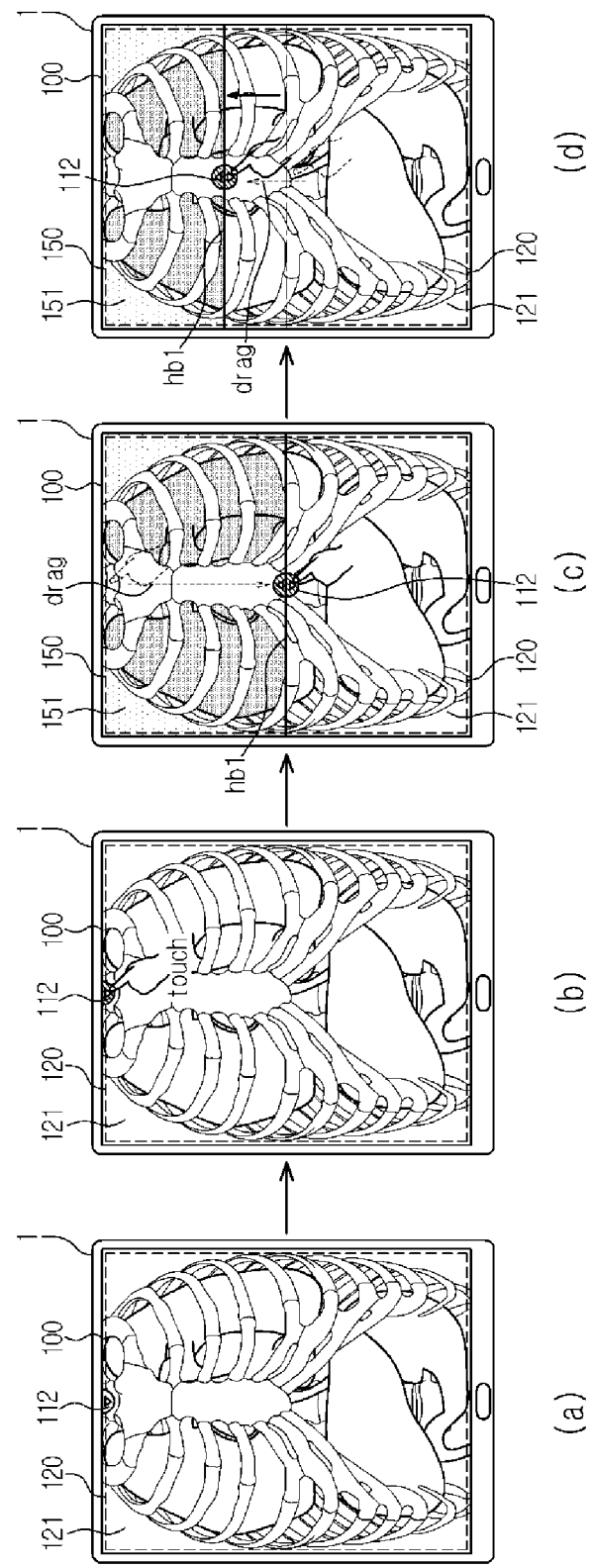

FIG. 10 illustrates another exemplary process for horizontally dividing the screen of the display unit. The exemplary embodiment illustrated in FIG. 10 differs from the exemplary embodiment of FIG. 9 in that the marker 112 of the display unit 100 is touched by using a touch tool, such as a finger or a touch pen. The display unit 100 may use any one or more of various kinds of commonly known touchscreens in order to facilitate input of a command by touch. Other technical details except this difference are the same as those of the exemplary embodiment of FIG. 9, and thus a description thereof will be omitted.

FIGS. 11, 12, 13, and 14 illustrate another exemplary embodiment for dividing the screen of the display unit.

Figure 11:
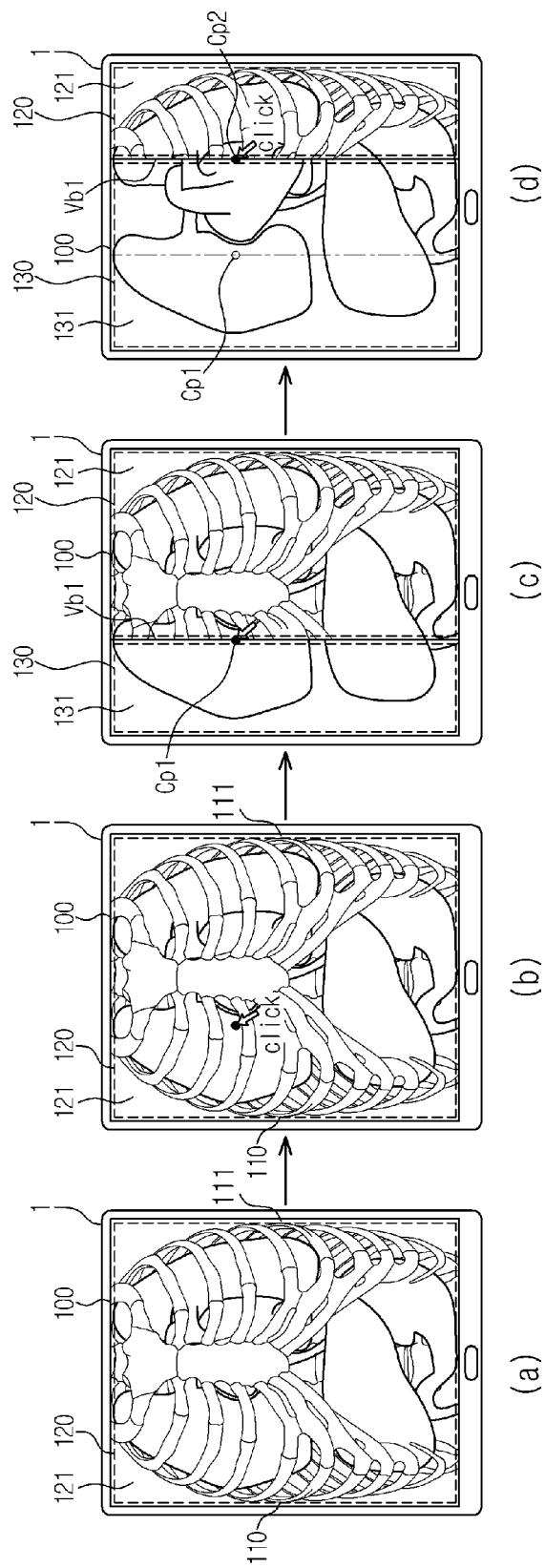

Referring to drawing (a) of FIG. 11, the display unit 100 displays a general x-ray image which is obtained by photographing the chest region of the object, and a separate marker which is usable to divide the screen is not shown.

When any position on the screen is clicked as shown in drawing (b) of FIG. 11, a vertical boundary line vb1 which passes through the click point cp1 is created, as shown in drawing (c) of FIG. 11. The screen is divided into the first region 120 and the second region 130 by the vertical boundary line vb1 which is created as the boundary. While the boundary line vb1 between the first region 120 and the second region 130 is illustrated as being vertical, the boundary line may be horizontal or diagonal. To enable the user to select a desired boundary line, different manipulations for selection of respective boundary lines may be predetermined and stored. For example, manipulations may be predetermined such that a vertical boundary line is created when the click point cp1 is clicked once, and a horizontal boundary line is created when the click point cp1 is clicked twice. The images of the object displayed in the first region 120 and the second region 130 which are created by dividing the screen are the same as those described above with reference to FIG. 2, and thus a description thereof will be omitted.

In this exemplary embodiment, the screen shares of the first region 120 and the second region 130 may be adjusted simply by clicking the point cp1 at which creation of a boundary line vb1 is desired, in contrast with the exemplary embodiment of FIG. 2 in which the screen shares of the first region 120 and the second region 130 are adjusted by dragging a marker. More specifically, when a point cp2 which is different from the click point cp1 is clicked, as shown in drawing (d) of FIG. 11, the vertical boundary line vb1 shown in drawing (c) of FIG. 11 disappears, and a new vertical boundary line vb1 which passes through the click point cp2 is created. Thereby, the screen is divided into the first region 120 and the second region 130 by the new vertical boundary line vb1 which has been created as the boundary. Compared to drawing (c) of FIG. 11, the screen share of the first region 120 decreases and the screen share of the second region 130 increases in drawing (d) of FIG. 11.

As shown in drawing (d) of FIG. 11, when the new click point cp2 is clicked once, the new vertical boundary line vb1 which passes through the new click point cp2 is created. Although not separately shown, when the new click point cp2 is kept clicked, a new vertical boundary line vb1 may be created in such a manner that the vertical boundary line vb1 shown in drawing (c) of FIG. 11 shifts to the position of the vertical boundary line vb1 shown in drawing (d) of FIG. 11.

Figure 12:
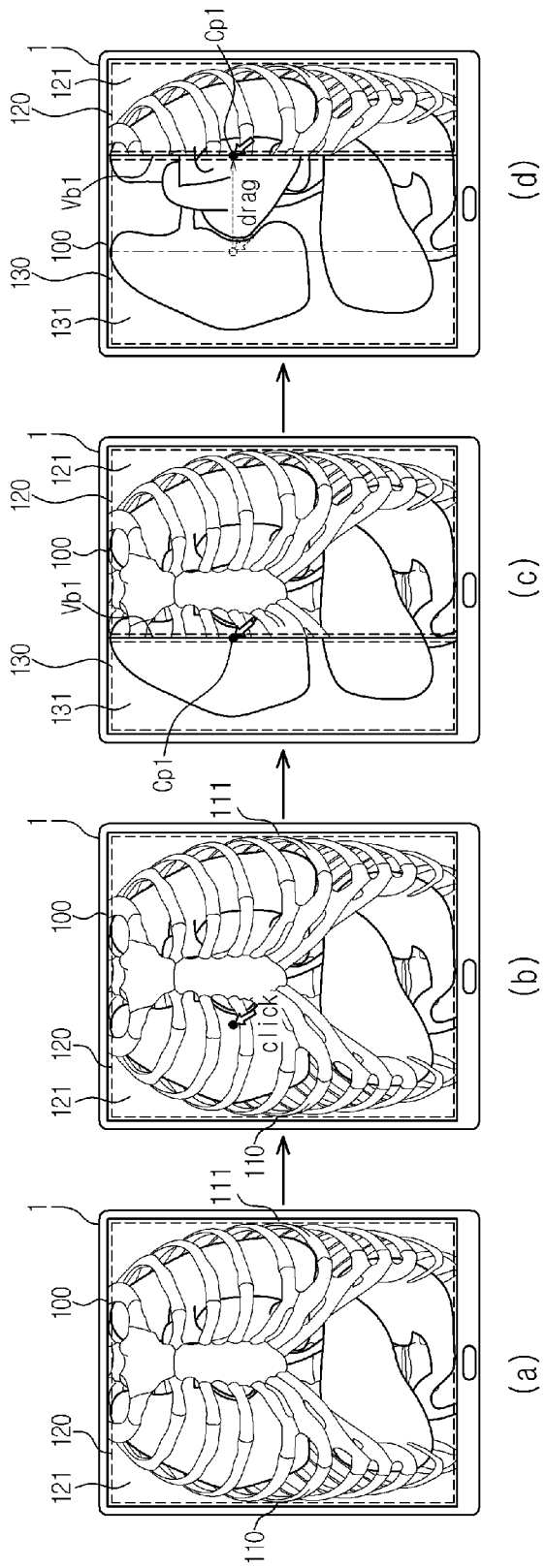

Unlike the method illustrated in FIG. 11, a new vertical boundary line vb1 may be created, as shown in drawing (d) of FIG. 12, in such a manner that the vertical boundary line vb1 shown in drawing (c) of FIG. 12 shifts to the position of the vertical boundary line vb1 shown in drawing (d) of FIG. 12 along a cursor which is dragged from the click point cp1 shown in drawing (c) of FIG. 12 to the click point cp1 shown in drawing (d) of FIG. 12. In particular, in this exemplary embodiment, a new click point cp2 is not created as in drawing (d) of FIG. 11, but the click point cp1 shown in drawing (c) of FIG. 12 is shifted to create a boundary line.

Figure 13:
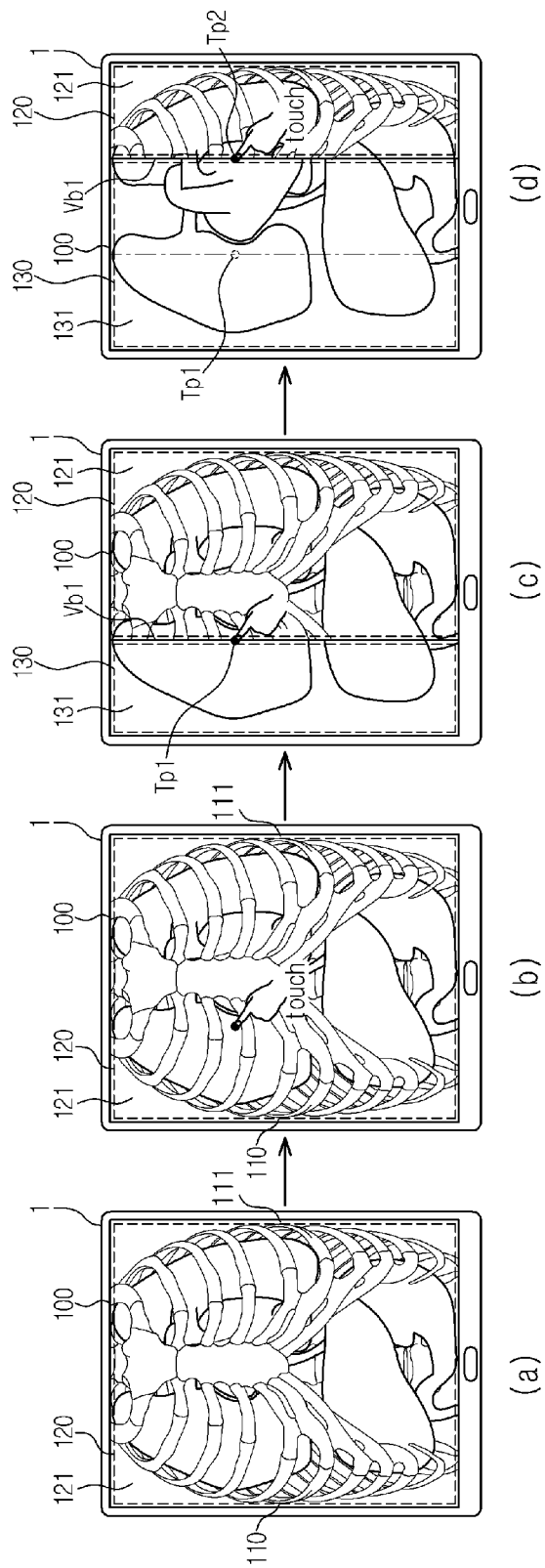
Figure 14:
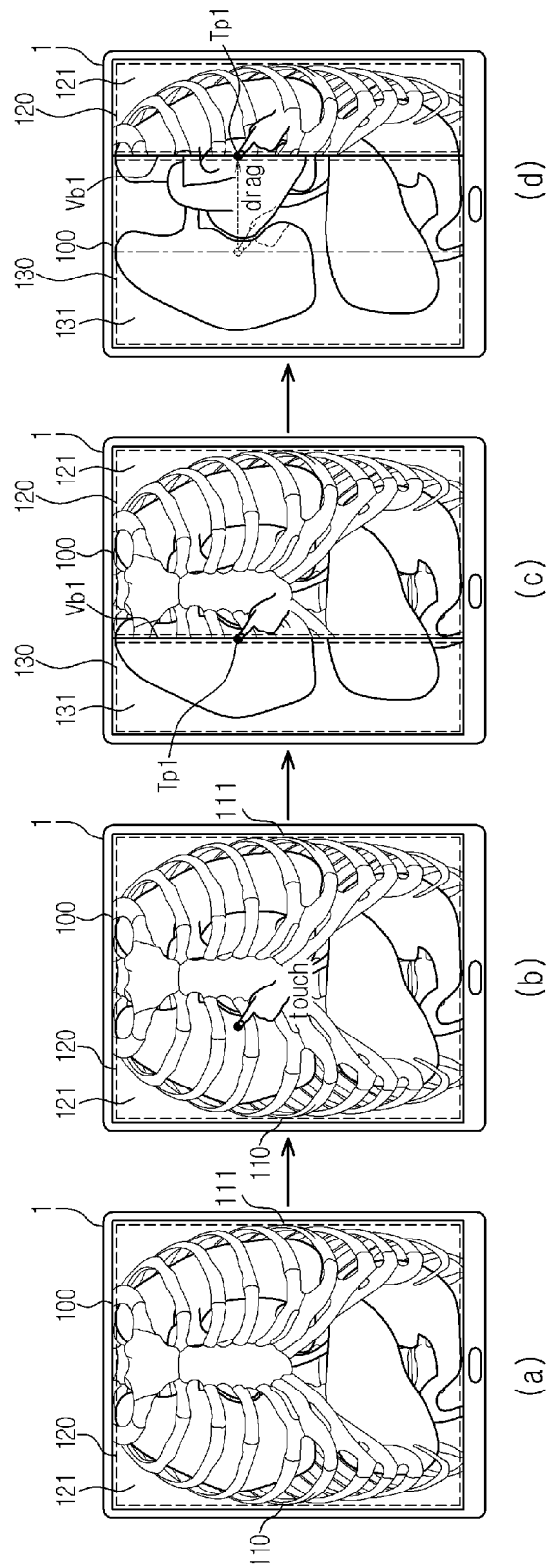

FIGS. 13 and 14 respectively illustrate dividing the screen into the same regions as in FIGS. 11 and 12, respectively. Unlike FIGS. 11 and 12, dividing is performed by touch. The exemplary embodiment illustrated in FIGS. 13 and 14 differs from the exemplary embodiment of FIGS. 11 and 12 in that the display unit 100 is touched using a touch tool, such as a finger or a touch pen. The display unit 100 may use any one or more of various kinds of commonly known touchscreens in order to facilitate input of a command by touch. Other technical details except this difference are the same as those of the exemplary embodiment of FIGS. 11 and 12, and thus a description thereof will be omitted.

Unlike FIGS. 2 through 14, which illustrate that various kinds of images acquired through an x-ray apparatus are displayed in the first region 120 and the second region 130, images which are acquired by photographing the same region of the same object by using different kinds of modalities may be displayed in the first region 120 and the second region 130. For example, the same lateral cross section of a brain is photographed by using computed tomography (CT) and positron emission tomography (PET). Then, the image captured via CT may be displayed in the first region 120, and the image captured via PET may be displayed in the second region 130. In this case, the user is able to seamlessly check several images of the same region of the same object which have been photographed by using different modalities on one single display apparatus, and therefore, a more efficient and accurate diagnosis may be possible.

Figure 15:
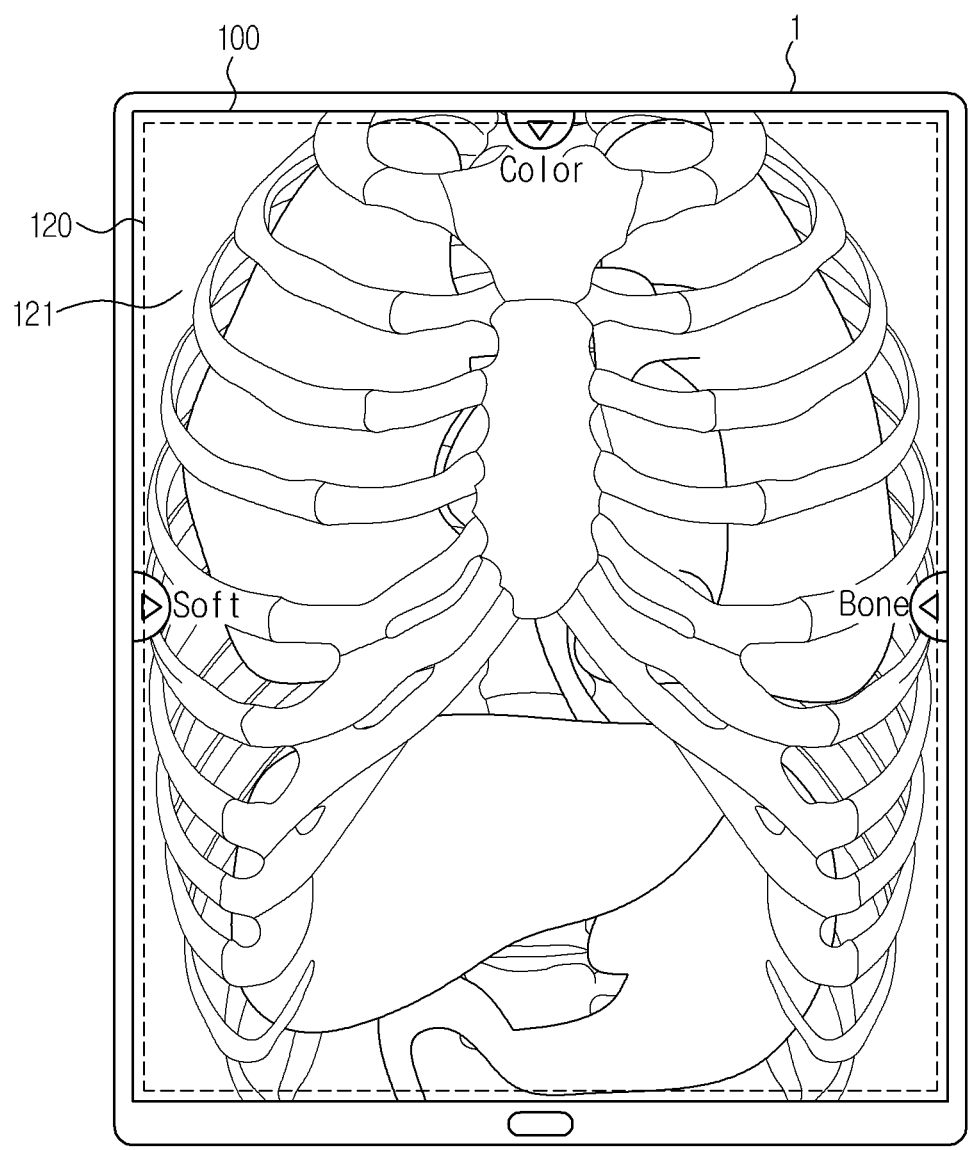
FIG. 15 is a view which illustrates an example of displaying a marker and a text together on a display unit in order to facilitate pre-checking of an image displayed on a divided region.

FIG. 15 is a view which illustrates an example of displaying a marker and text together on the display unit.

In the case that the markers 110, 111 and 112 displayed on the display unit 100 are moved, text indicating respective features of different images 131, 161 and 151 is also displayed on the screen of the display unit 100 in order to inform the user regarding the different types of images of an object which are respectively displayed in the different regions 130, 160 and 150 of the divided screen (see FIGS. 7, 8, 9, and 10).

As shown in FIG. 15, the text "soft" and the marker 110 are displayed together on the left side of the display unit 100 such that the user is informed that a soft tissue x-ray image is displayed in a region of the screen when the marker 110 is moved. The text "bone" and the marker 111 are displayed together on the right side of the display unit 100 such that the user is informed that a bone x-ray image is displayed in a region of the screen when the marker 111 is moved. In addition, the text "color" and the marker 112 are displayed together on the upper side of the display unit 100 such that the user is informed that a color x-ray image is displayed in a region of the screen when the marker 112 is moved.

Displaying the texts and the markers 110, 111 and 112 together is simply an example. Alternatively, thumbnails and the markers 110, 111 and 112 may be displayed together. Any type of marking which indicates the types of images displayed in the regions 130, 160 and 150 is within the scope of this exemplary embodiment.

FIGS. 16, 17, 18, 19, and 20 are views which illustrate exemplary embodiments of changing a first image and a second image, which are respectively displayed in the first region and the second region that have been divided from each other, to other images.

Figure 16:
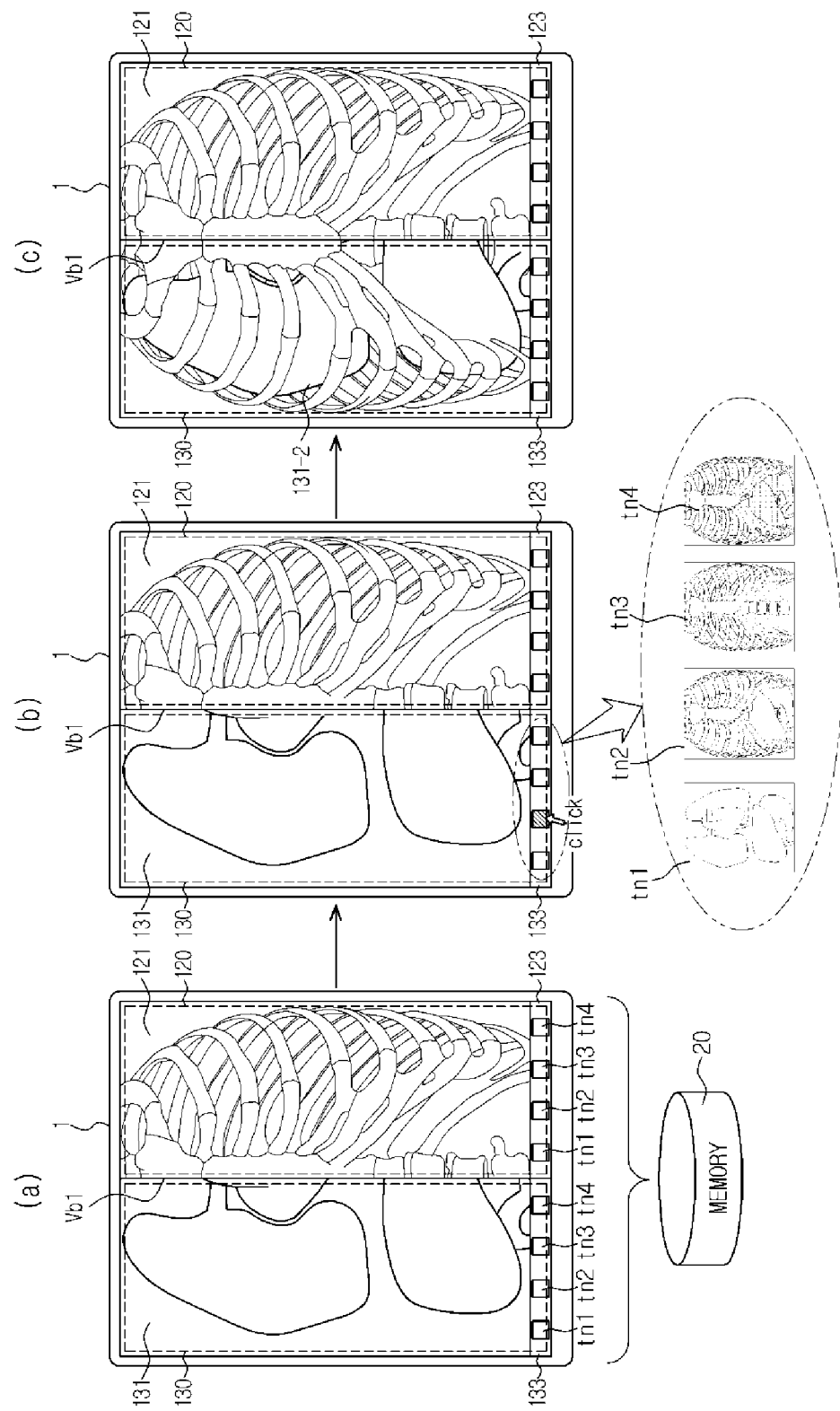
FIGS. 16, 17, 18, 19, and 20 are views which illustrate an exemplary method for changing an image which is displayed in a region of the divided screen to a different image type.

Referring to FIG. 16, windows 123 and 133 which relate to displaying a plurality of thumbnails tn1, tn2, tn3 and tn4 may be respectively formed at the lower ends of the first region 120 and the second region 130. The windows 123 and 133 which relate to displaying the thumbnails tn1, tn2, tn3 and tn4 may be formed not only at the lower ends of the regions, but also at other positions, such as the upper ends of the regions, or at other suitable positions. The thumbnails tn1, tn2, tn3 and tn4 may include thumbnails of x-ray images of the same region of an object which have captured by using various techniques. The x-ray images represented by the thumbnails tn1, tn2, tn3 and tn4 may be pre-stored in the memory 20 (see FIG. 1). Various thumbnails of the x-ray images, such as the thumbnail tn1 of a soft tissue x-ray image, the thumbnail tn2 of a general x-ray image, the thumbnail tn3 of a bone x-ray image, and/or the thumbnail tn4 of a color x-ray image, may be displayed.

Figure 17:
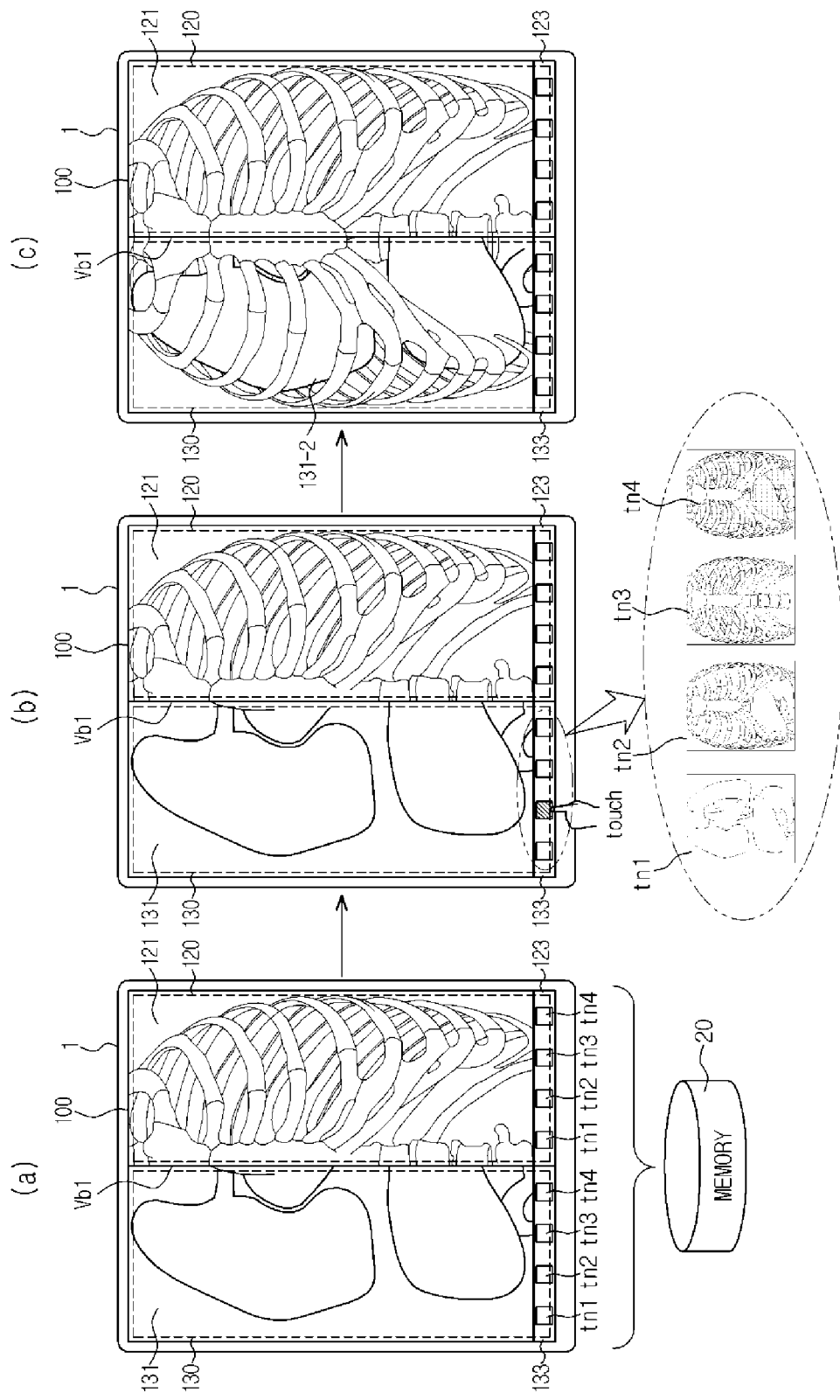

Referring to drawing (b) of FIG. 16 and drawing (b) of FIG. 17, a bone x-ray image is displayed in the first region 120, and a soft tissue x-ray image is displayed in the second region 130. In order to compare the general x-ray image with the bone x-ray image, the user may click or touch the thumbnail tn2 of the general x-ray image among the thumbnails tn1, tn2, tn3 and tn4 displayed at the lower end of the second region 130. Once the thumbnail tn2 of the general x-ray image is clicked or touched, the soft tissue x-ray image displayed in the second region 130 changes to the general x-ray image. The changed general x-ray image and the bone x-ray image in the first region 120 naturally match with each other at the boundary line vb1, and the image produced by the match shows the same region of the same object.

Although not shown in the figures, in order to compare the soft tissue x-ray image with the color x-ray image, the user may click or touch the thumbnail tn4 of the color x-ray image among the thumbnails tn1, tn2, tn3 and tn4 displayed at the lower end of the first region 120. Once the thumbnail tn4 of the color x-ray image is clicked or touched, the bone x-ray image displayed in the first region 120 is changed to the color x-ray image. The changed color x-ray image and the general x-ray image in the second region 130 naturally match with each other at the boundary line vb1, and the image produced by the coordination shows the same region of the same object.

Figure 18:
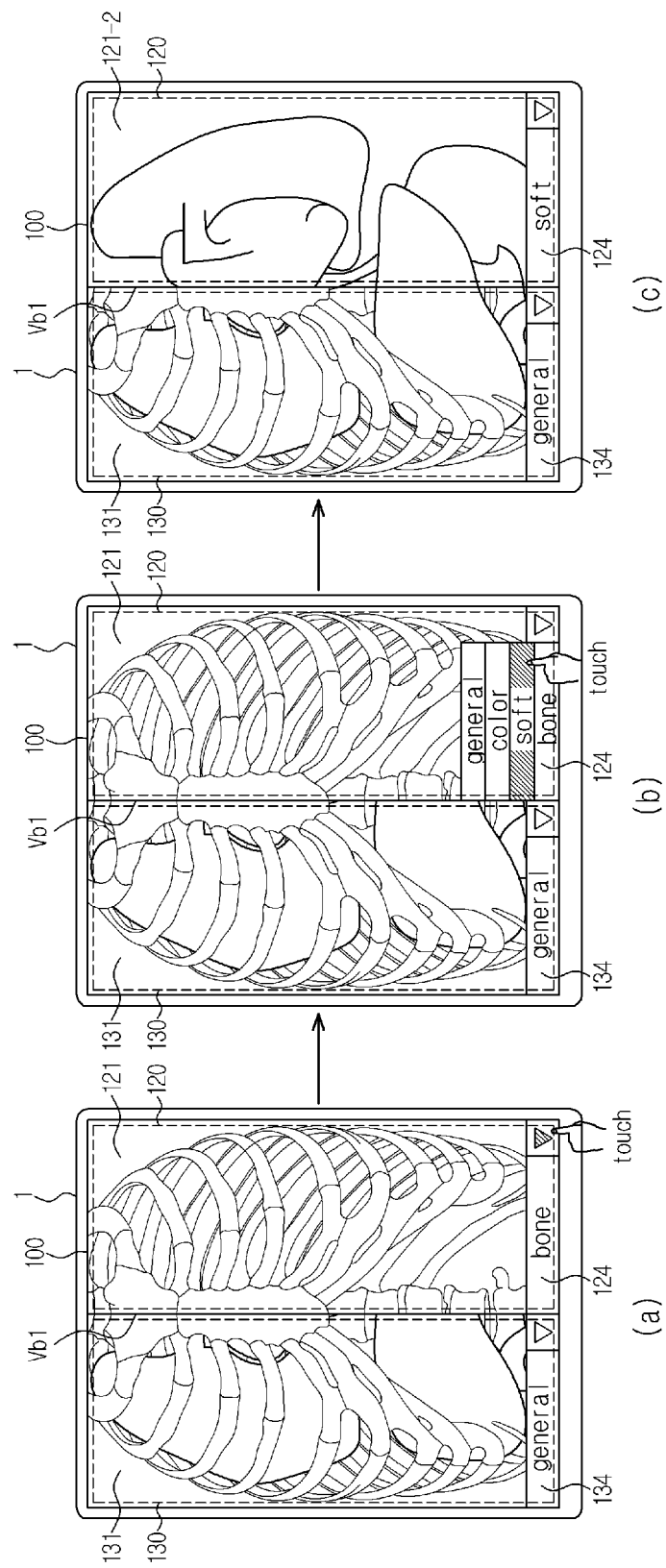

Referring to FIG. 18, windows 124 and 134 which relate to displaying text which indicates the feature of a corresponding x-ray image to be displayed in a corresponding one of the respective regions and an icon for change of the text together may be formed at the lower ends of the first region 120 and the second region 130. The windows 124 and 134 which relate to displaying text may be formed not only at the lower ends of the regions, but also at other positions, such as the upper ends of the regions, or any other suitable positions.

In the case that the first image 121 which is displayed in the first region 120 is to be changed from the bone x-ray image to the soft tissue x-ray image, the user touches or clicks an icon for change of text in the window 124, 134 formed at the lower end of the first region 120 as shown in drawing (a) of FIG. 18, and then touches or clicks text "soft" as shown in drawing (b) of FIG. 18. Upon touching or clicking the text, the first image 121 which is displayed in the first region 120 changes from the bone x-ray image to the soft tissue x-ray image, as shown in drawing (c) of FIG. 18. The changed soft tissue x-ray image and the general x-ray image in the second region 130 naturally match with each other at the boundary line vb1, and the image produced via the match shows the same region of the same object.

Figure 19:
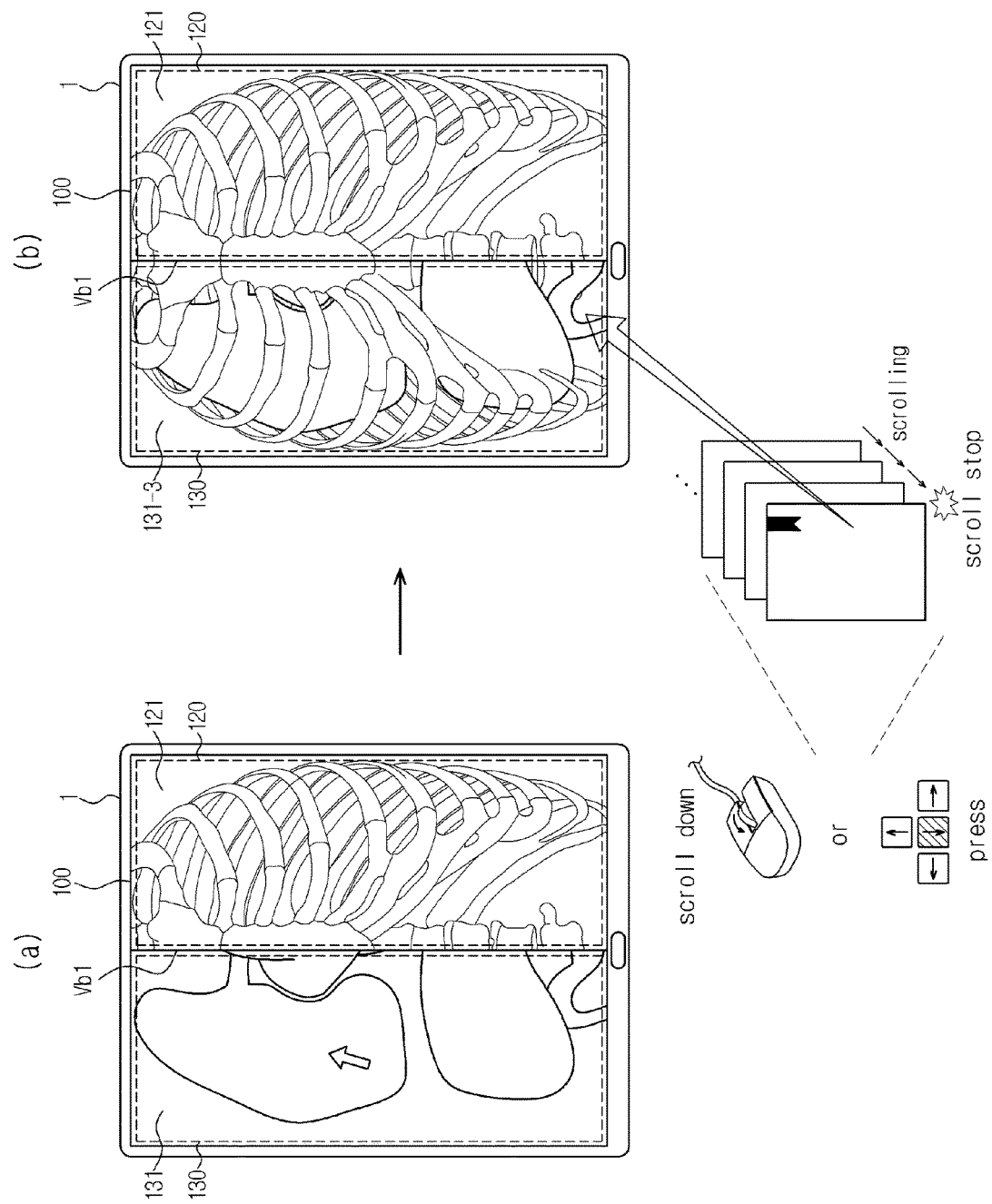
Figure 20:
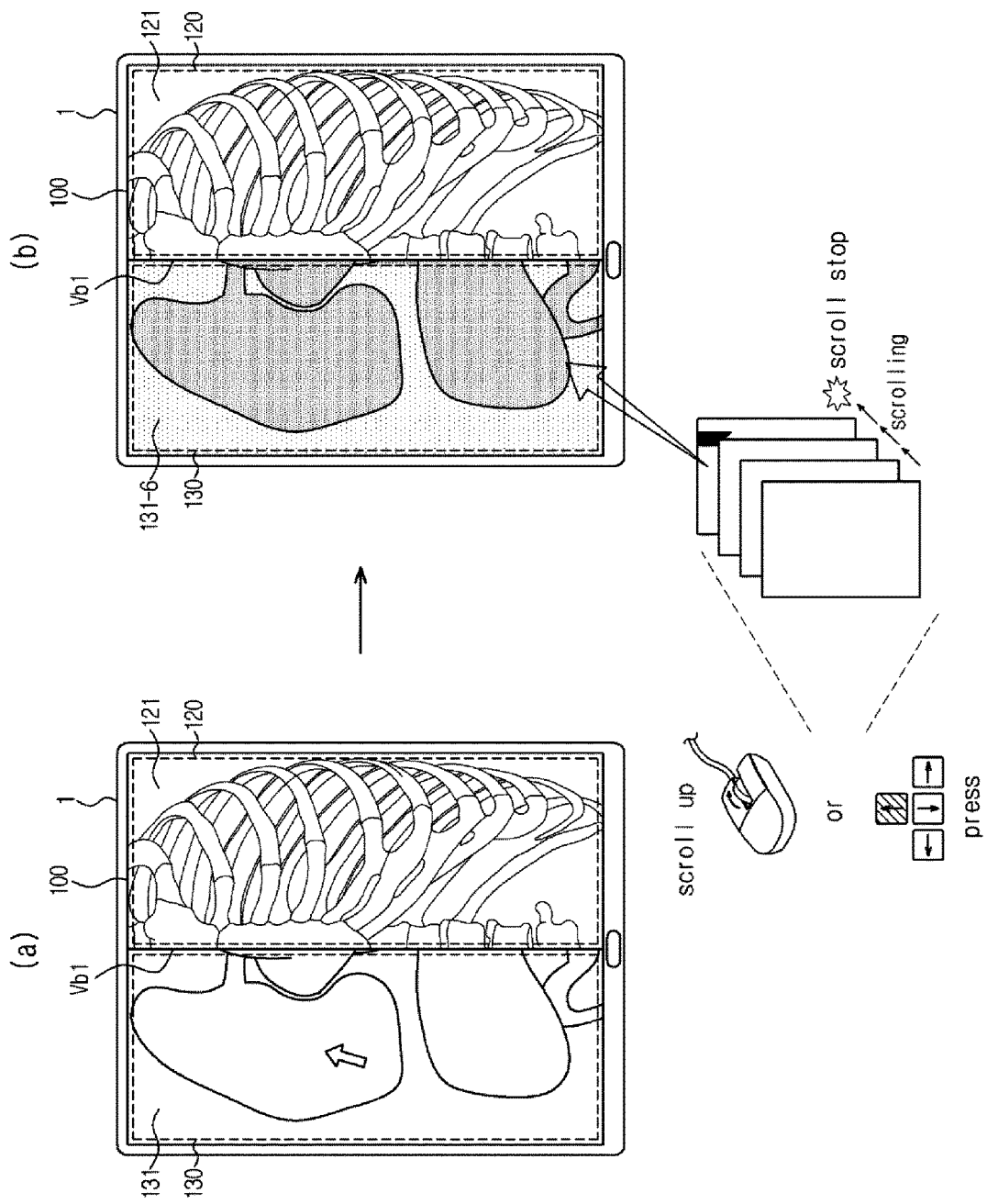

Referring to FIGS. 19 and 20, a separate window which relates to displaying a thumbnail or text is not formed at the first region 120 and the second region 130. In this exemplary embodiment, an image may be changed by positioning a mouse in the region where the image is displayed, and then inputting a scroll command via the wheel of the mouse, or inputting a command via manipulation of arrow keys on a keyboard. Alternatively, similar to a result of inputting a scroll command via the wheel of the mouse, an image may be changed by touching the region within which the image is displayed and dragging up or down the same.

As shown in FIGS. 19 and 20, when the cursor is positioned in the second region 130 and a scroll-down command is inputted by rolling down the wheel of the mouse, the second image 131 which is displayed in the second region 130 is sequentially changed to each of the x-ray images stored in the memory 20. In the case that a desired image is skipped, the user may find the desired image by inputting a scroll-up command by rotating the mouse upward. When the desired image is displayed in the second region 130 as a result of continuous input of the scroll-down command or scroll-up command until the scrolling is stopped, the image is not changed any more.

The user may change the image which is displayed in the second region 130 not only by inputting a command via the mouse, but also by manipulating an arrow key indicating the downward direction or the upward direction among the arrow keys on the keyboard in the same manner. The image may be changed by manipulating the left arrow and right arrow keys. The illustrated mouse and keyboard are exemplary, and the image may be changed using other input methods, as described above. In addition, without using a separate input unit such as a mouse or a keyboard, the user may change the image which is displayed in the second region 130 by directly touching the screen of the display unit 100 and dragging up or down the same with a finger or a touch pen.

Figure 21:
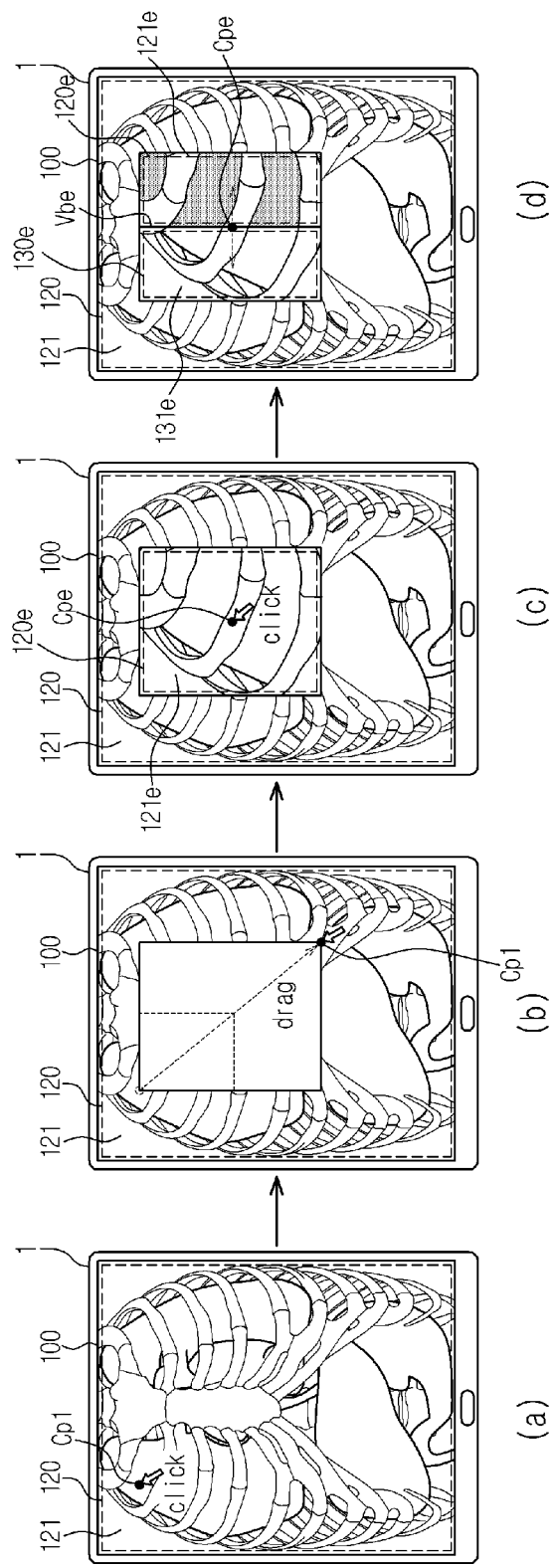
FIGS. 21 and 22 are views which illustrate an exemplary method of enlarging and dividing an image which is displayed on the display unit.
Figure 22:
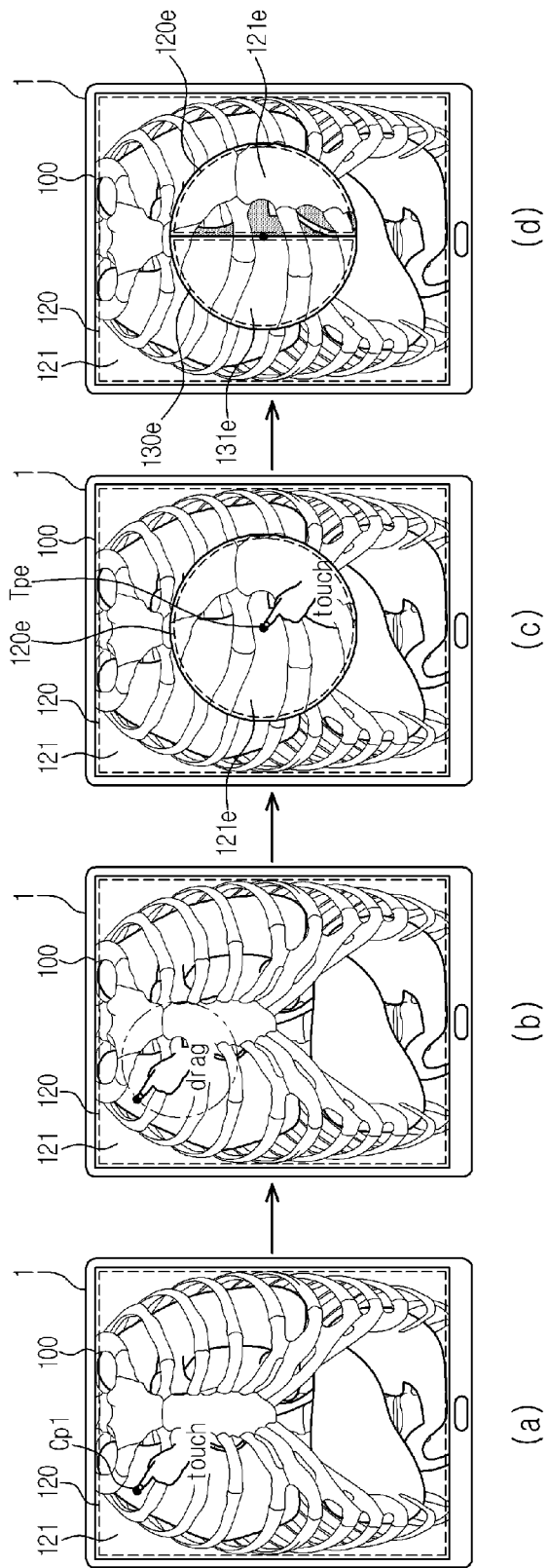

FIGS. 21 and 22 illustrate an exemplary method of enlarging and dividing an image which is displayed on the display unit. Referring to FIG. 21, the user may input a command which relates to enlarging a region of interest in order to observe the region of interest by enlarging the region. As shown in drawings (a) and (b) of FIG. 21, an area to be enlarged is specified by clicking a predetermined position near the region of interest and dragging the same. In this process, a rectangle for which the drag line serves as a diagonal line thereof is generally created in the dragging direction. The rectangular area created in this way is specified as the enlargement area.

The shape and size of the enlargement region may be directly specified by touch rather than by clicking. For example, as shown in drawings (a) and (b) of FIG. 22, a predetermined position near the region of interest is touched, and the shape of an area to be enlarged is drawn with a finger or a touch pen. In drawing (b) of FIG. 22, an enlargement area having a circular shape is created. The method for specifying an enlargement area which is illustrated in FIGS. 21 and 22 is purely exemplary, and specifying an enlargement area may be implemented by using any one or more of various methods.

As shown in drawing (c) of FIG. 21 and drawing (c) of FIG. 22, once an enlargement area is specified, the image of a portion which corresponds to the enlargement area prior to specifying of the enlargement area is enlarged by a predetermined magnification factor and then displayed. The magnification factor may be preset in any one or more of various manners and stored the memory 20, and the user may select a desired magnification factor and determine an extent of enlargement of an image.

As described above with respect to several exemplary embodiments, the screen of the enlargement area may also be divided. In addition, images of the same region of an object which have been captured by using different respective techniques may be respectively displayed in the divided regions. Referring to drawing (d) of FIG. 21 and drawing (d) of FIG. 22, when any location on the screen is clicked or touched, a vertical boundary line vbe which passes through a click point cpe or a touch point tpe is created, and the screen is divided into a first region 120e and a second region 130e by the created boundary line. While the boundary line vbe between the first region 120e and the second region 130e is illustrated as being vertically created, a horizontal line or a diagonal line may alternatively be created as the boundary line. In order to enable the user to select a desired boundary line, different manipulations which correspond to selections of respective boundary lines may be predetermined and stored. For example, manipulations may be predetermined such that a vertical boundary line is created when the click point is clicked once, and a horizontal boundary line is created when the click point is clicked twice. The enlargement area may also be divided by dragging the markers 110 and 111 which are displayed in the enlargement area, similarly as illustrated in FIG. 2.

Images of the same region of an object which are captured by using different respective techniques are respectively displayed in the first region 120e and the second region 130e divided by the boundary. As shown in drawing (d) of FIG. 21 and drawing (d) of FIG. 22, a color x-ray image may be displayed in the first region 120e, and a general x-ray image may be displayed in the second region 130e. In order to adjust the relative screen shares of the first region 120e and the second region 130e, the markers 110 and 111 may be dragged, as illustrated in FIG. 2, or a point in an enlargement area at which the boundary line vbe is desired to be created may be clicked or touched, as illustrated in FIGS. 11 through 14.

Even when the relative screen shares of the first region 120e and the second region 130e vary and thus the proportional amounts of the region of an object shown in the first image 121e and the second image 131e vary, the first image 121 and the second image 131e always match with each other at the vertical boundary line vbe, regardless of changes in the respective proportional amounts shown in the first image 121e and the second image 131e. In addition, the method illustrated in FIGS. 16 through 20 may be applied to the first image 121e and the second image 131e as respectively displayed in the first region 120e and the second region 130e, which regions are created by dividing the enlargement area so as to change the images into different types of images.

According to the various exemplary embodiments described above, a user can easily and quickly check different images of a certain region of an object in an alternating manner. In addition, the user can seamlessly display and compare different respective types of images of a certain region of an object, which images are captured by using correspondingly different techniques, thus obtaining unique information respectively on one display apparatus, rather than on multiple display apparatuses by combining the images. Because multiple images of the same object region are simultaneously checked on one display apparatus, a resulting accuracy of diagnosis may be enhanced, and more intuitive diagnosis may be possible.

As is apparent from the above description, according to exemplary embodiments, different respective types of images with unique respective information which are captured by using different techniques may be compared with each other on one display apparatus, rather than on multiple display apparatuses.

In addition, it may be possible to simultaneously check multiple images of a region of interest on one display apparatus, and therefore an accuracy of diagnosis may be enhanced, and more intuitive diagnosis may be possible.

Although a few exemplary embodiments have been shown and described, it will be appreciated by those of skill in the art that changes may be made to the exemplary embodiments without departing from the principles and spirit of the present inventive concept, the scope of which is defined in the claims and their equivalents.

What is claimed is:
1. A medical imaging apparatus comprising:
 a memory configured to store a plurality of X-ray images of a same region of an object;
 a display; and
 a processor configured to:
  control the display to display a first X-ray image from among the plurality of X-ray images;
  receive a first user selection to set a first area of the first X-ray image;

control the display to display a menu including a plurality of X-ray image types corresponding to the plurality of X-ray images stored in the memory;

in response to a second user selection to select one of the plurality of X-ray image types, control the display to change the first area of the first X-ray image to the first area of a second X-ray image, from among the plurality of X-ray images, corresponding to the selected X-ray image type, and to display a second area of tire first X-ray image together with the first area of the second X-ray image, the second area and the first area constituting an entire area of the first X-ray image;

in response to a first user instruction to enlarge the first area of the second X-ray image, control the display to display the enlarged first area of the second X-ray image, and to display the second area that is reduced as the first area is enlarged, of the first X-ray image; and in response to a second user instruction to shift the first area of the second X-ray image, control the display to display the shifted first area of the second X-ray image, and to display the second area that is shitted as the first area is shifted, of the first X-ray image.

2. The medical imaging apparatus according to claim 1, further comprising an input device configured to receive at least one from among the first user selection, the second user selection, the first user instruction and the second user instruction.

3. The medical imaging apparatus according to claim 1, wherein the display is further configured to receive a touch input related to at least one from among the first user selection, the second user selection, the first user instruction and the second user instructions.

4. The medical imaging apparatus according to claim 1, wherein the first area of the first X-ray image corresponds to a region of interest included in the first X-ray image.

5. The medical imaging apparatus according to claim 1, wherein the first area of the first X-ray image and the first area of the second X-ray image indicate a same part of the object.

6. The medical imaging apparatus according to claim 1, wherein a size of she first area of the second X-ray image corresponds to a size of the region of interest included in the displayed first X-ray image.

7. The medical imaging apparatus according to claim 1, wherein the controller Is further configured to control the display to display a text indicating a type of the second X-ray image, together with the second X-ray image.

8. The medical imaging apparatus according to claim 1, wherein the second X-ray image includes any one or any combination of a color X-ray image, a soft tissue X-ray image, and a bone X-ray image.

9. The medical imaging apparatus according to claim 1, wherein the plurality of X-ray images include a plurality of X-ray material images based on a plurality of corresponding X-ray energy bands.

10. A method of controlling a medical imaging apparatus comprising a memory configured to store a plurality of X-ray images of a same region of an object, a display and a processor, the method comprising:

controlling the display to display a first X-ray image from among the plurality of X-ray images;

receiving, a first, user selection to set a first area of the first X-ray image, controlling the display to display a menu including a plurality of X-ray image types corresponding to the plurality of X-ray images stored in the memory;

in response to a second user selection to select one of the plurality of X-ray image types, controlling, the display to change the first area of the first X-ray image to the first area of a second X-ray image, from among the plurality of X-ray images, corresponding to the selected X-ray image type and to display a second area of the first X-ray image together with the first area of the second X-ray image, the second area and the first area constituting entire area of the first X-ray image;

in response to a first user instruction to enlarge the first area of the second X-ray image, controlling the display to display the enlarged first area of the second X-ray image, and to display the second area that is reduced as the first area Is enlarged, of the first X-ray image; and in response to a second user instruction to shift the first area of the second X-ray image, controlling the display to display the shitted first area of the second X-ray Image, and to display the second area that is shifted as the first area is shifted, of the first X-ray image.

* * * * *